United States Patent
Craig et al.

(10) Patent No.: US 10,752,948 B2
(45) Date of Patent: Aug. 25, 2020

(54) ALPHA-HEMOLYSIN VARIANTS

(71) Applicant: Roche Sequencing Solutions, Inc., Pleasanton, CA (US)

(72) Inventors: Timothy Kellogg Craig, Campbell, CA (US); Cynthia Ann Cech, Newcastle, WA (US); Michael Dorwart, Mountain View, CA (US); Liv Elisabeth Jensen, Palo Alto, CA (US); Marshall Winston Porter, Santa Clara, CA (US); Christos Tzitzilonis, Mountain View, CA (US); Alexander Hyun-min Yang, Campbell, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

(21) Appl. No.: 16/238,874

(22) Filed: Jan. 3, 2019

(65) Prior Publication Data
US 2019/0119745 A1     Apr. 25, 2019

Related U.S. Application Data

(63) Continuation of application No. 15/274,770, filed on Sep. 23, 2016, now Pat. No. 10,227,645.

(60) Provisional application No. 62/232,175, filed on Sep. 24, 2015, provisional application No. 62/244,852, filed on Oct. 22, 2015.

(51) Int. Cl.
*C07K 14/31*     (2006.01)
*C12Q 1/6869*    (2018.01)

(52) U.S. Cl.
CPC ............ *C12Q 1/6869* (2013.01); *C07K 14/31* (2013.01)

(58) Field of Classification Search
CPC ...................................................... C07K 14/31
See application file for complete search history.

(56) References Cited

U.S. PATENT DOCUMENTS

2017/0088588 A1   3/2017   Dorwart

FOREIGN PATENT DOCUMENTS

| WO | 1999005167 A1 | 2/1999 |
| WO | 2013123450 A1 | 8/2013 |
| WO | 2014074727 A1 | 5/2014 |
| WO | 2014100481 A2 | 6/2014 |
| WO | 2015016125    | 2/2015 |
| WO | 2015055981 A2 | 4/2015 |
| WO | 2015061510 A1 | 4/2015 |
| WO | 2016069806 A2 | 5/2016 |

OTHER PUBLICATIONS

Maria Fyta, "Threading DNA through nanopores for biosensing applications", Journal of Physics: Condensed Matter, Institute of Physics Publishing, Bristol, GB, vol. 27, No. 27, doi:10.1088/0953-8984/27/27/273101, ISSN 0953-8984, (Jun. 10, 2015), p. 273101, (Jun. 10, 2015), XP020287187.

Walker Barbara et al, "Key residues for membrane binding, oligomerization, and pore forming activity of staphylococcal alpha-hemolysin identified by cysteine scanning mutagenesis and targeted chemical modification", Journal of Biological Chemistry, American Society for Biochemistry and Molecular Biology, US, (Sep. 29, 1995), vol. 270, No. 39, doi:10.1074/JBC.270.39.23065, ISSN 0021-9258, pp. 23065-23071, XP002547872.

Akeson et al., "Microsecond time-scale discrimination among polycytidylic acid, polyadenylic acidand polyuridylic acid as homopolymers or as segments within single RNA molecules", Biophys J. Dec. 1999;77(6):3227-33.

Aksimentiev et al., "Imaging a-Hemolysin with Molecular Dynamics: Ionic Conductance, Osmotic Permeability, and the Electrostatic Potential Map", Biophys J. Jun. 2005;88(6):3745-61. Epub Mar. 11, 2005.

Bhattacharya et al. "Rectification of the Current in α-Hemolysin Pore Depends on the Cation Type: The Alkali Series Probed by Molecular Dynamics Simulations andExperiments", The Journal of Physical Chemistry (2011), vol. 115, Issue 10, pp. 4255-4264.

Butler et al., "Single-molecule DNA detection with an engineered MspA protein nanopore", Proc Natl Acad Sci USA. Dec. 30, 2008;105(52):20647-52. Epub Dec. 19, 2008.

Dennler et al., Transglutaminase-based chemo-enzymatic conjugation approach yields homogenous antibody-drug conjugates, Bioconjug Chem 25:569-578 (2014).

GenScriptatwww.genscript.com/molecular-biology-glossary/9181/ Concatemer, 2018.

Hammerstein et al., Subunit dimers of a-Hemolysin Expand the Engineering Toolbox for Protein nanopores, J. Biol. Chem. (2011)286:14324-14334.

Heck et al., Enzyme-catalyzed protein crosslinking, Appl Microbiol Biotechnol 97:461-475 [2013].

Howorka et al., "Kinetics of duplex formation for individual DNA strands within a single protein nanopore", Proc Natl Acad Sci U S A. Nov. 6, 2001;98(23):12996-3001. Epub Oct. 23, 2001.

Howorka et al., "Sequence-specific detection of individual DNA strands using engineered nanopores, Nature Biotechnology",Nat Biotechnol. Jul. 2001;19(7):636-9.

Jursch et al. 1994; Histidine residues near the N-terminus of Staphylococcal alpha-toxin as reporters of regions that are critical for oligomerization and pore formation. Infection and Immunity. 62(6):2249-2256.

(Continued)

*Primary Examiner* — Karen Cochrane Carlson
(74) *Attorney, Agent, or Firm* — FisherBroyles, LLP; Jason M. Pass; Victoria L. Boyd

(57) ABSTRACT

Described herein are engineered alpha-hemolysin subunits having mutated oligomerization domains for assembling into heptameric nanopores in lipid bilayers.

25 Claims, 15 Drawing Sheets
Specification includes a Sequence Listing.

(56) References Cited

OTHER PUBLICATIONS

Kasianowicz et al., Nanometer-scale pores: potential applications for analyte detection and DNA characterization, Proc. Natl. Acad. Sci. USA (1996) 93:13770-13773.
Korchev et al., "Low Conductance States of a Single Ion Channel are not 'Closed'," J Membr Biol. Oct. 1995;147(3):233-9.
Krasilnikov et al., "Ion Transport Through Channels Formed in Lipid Bilayers by Staphylococcus aureus Alpha-Toxin", 1989, General Physiology and Biophysics, 8:213-222.
MedicineNet, at/www.medicinenet.com/script/main/art.asp?articlekey=24023, 2018.
Meller et al.,"Voltage-Driven DNA Translocations through a Nanopore", Phys Rev Lett. Apr. 9, 2001;86(15):3435-8.
Menzies et al. 1994; Site-directed mutatgenesis of the alpha-toxin gene of *Staphylococcus aureus*: Role of histidines in toxin activity in vitro and in a murine model. Infection and immunity. 62(5):1843-1847.
Movileanu et al., "Detecting protein analytes that modulate transmembrane movement of a polymer chain within a single protein pore", Nat Biotechnol. Oct. 2000;18(10):1091-5.
Nakane et al., "A Nanosensor for Transmembrane Capture and Identification of Single Nucleic Acid Molecules", Biophys J. Jul. 2004;87(1):615-21.
Noskov et al., "Ion Permeation through the α-Hemolysin Channel: Theoretical Studies Based on Brownian Dynamics and Poisson-Nernst-Plank Electrodiffusion Theory" Biophysical Journal (2004), vol. 87, issue 4, pp. 2299-2309.
PCT International Preliminary Report on Patentability dated Mar. 27, 2018 for PCT application No. PCT/EP2016/072220.
PCT International Search Report and Written Opinion dated Jan. 23, 2017 for PCT application No. PCT/EP2016/072220, 19 Pages.
Rashidian et al., Chemoenzymatic labeling of proteins: techniques and approaches, Bioconjug Chem 24:1277-1294 [2013].
Rhee and Burns, "Nanopore sequencing technology: nanopore preparations", Trends Biotechnol. Apr. 2007;25(4):174-81. Epub Feb. 22, 2007.
Sack et al., "How to Validate a Heteromeric Ion Channel Drug Target: Assessing Proper Expression of Concatenated Subunits", J. Gen. Physiology, vol. 131, Issue 5, pp. 415-420 (2008).
Science Direct at/www.sciencedirect.com/topics/neuroscience/concatemer, 2018.
Song et al., "Structure of Staphylococcal a-Hemolysin, a Heptameric Transmembrane Pore", Science. Dec. 13, 1996;274(5294):1859-66.
Thapa et al., Native Chemical Ligation: A boon to peptide chemistry, Molecules 19:14461-14483 [2014].
Walker et al. 1992; Assembly of the oligomeric membrane pore formed by Staphylococcal alpha-hemolysin examined by truncation mutagenesis. J. Biol. Chem. 267(30): 21782-21786.
What When How atwhat-when-how.com/molecular-biology/concatemers-molecular-biology, 2018.
Wikipedia, the free encyclopedia at: en.wikipedia.org/wiki/Concatemer, 2018.
Winters-Hilt, Stephen. "The α-Hemolysin nanopore transduction detector—single-molecule binding studies and immunological screening of antibodies and aptamers," BMC Bioinformatics, 8(Suppl 7):S9, 2007, 29 pages.
Wu and Guo, Sortase-mediated transpeptidation for site-specific modification of peptides, glycopeptides, and proteins, J Carbohydr Chem 31:48-66 [2012].
Yadav, Navneet Kumar et al. "Next Generation Sequencing: Potential and Application in Drug Discovery," The Scientific World Journal, vol. 2014, Article ID 802437, 7 pages.
Yegnasubramanian, Srinivasan. "Explanatory Chapter: Next Generation Sequencing," Methods Enzymol. 529: 201-208, 2013, 6 pages.
Zakeri et al, 2012, "Peptide tag forming a rapid covalent bond to a protein, through engineering a bacterial adhesion", PNAS, 109(12):E690-E697 w/supporting figs (19 pp.).
Berube, et al., "Staphylococcus aureus α-Toxin: Nearly a Century of Intrigue," Toxins 2013, 5,1140-1166; Published Jun. 13, 2013, www.mdpi.com/journal/toxins.

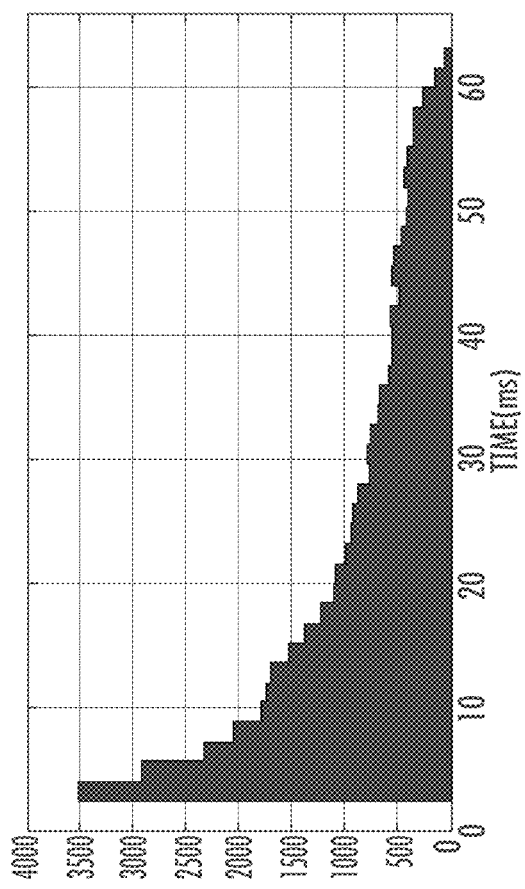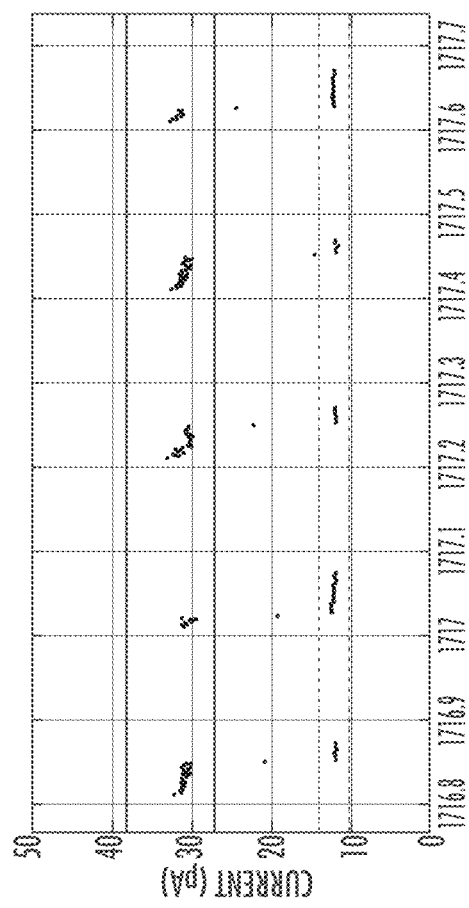
FIG. 1A
FIG. 1B

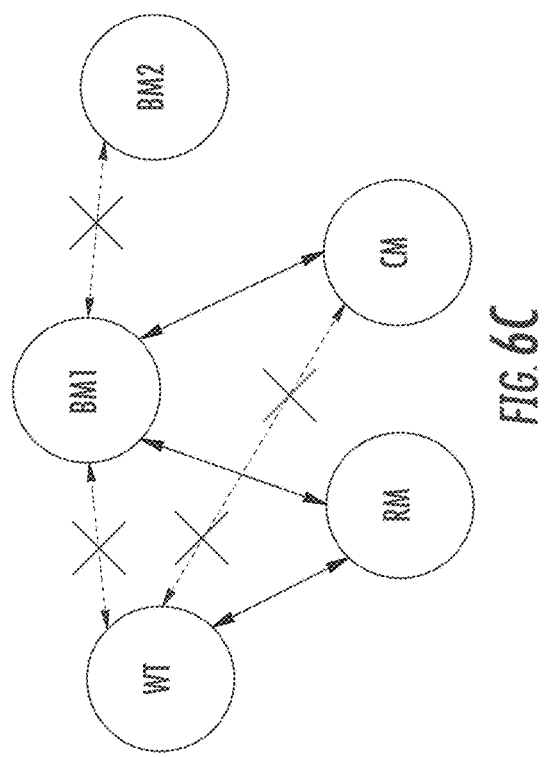
FIG. 6C
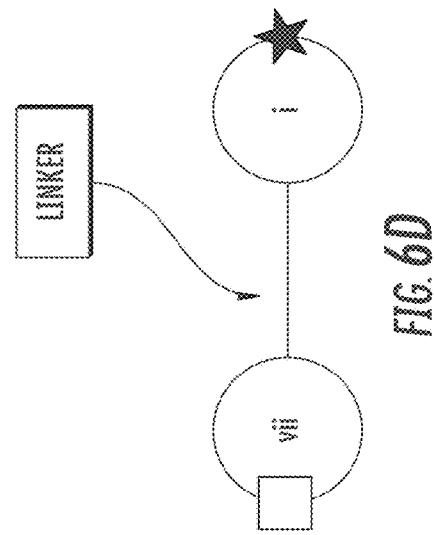
FIG. 6D
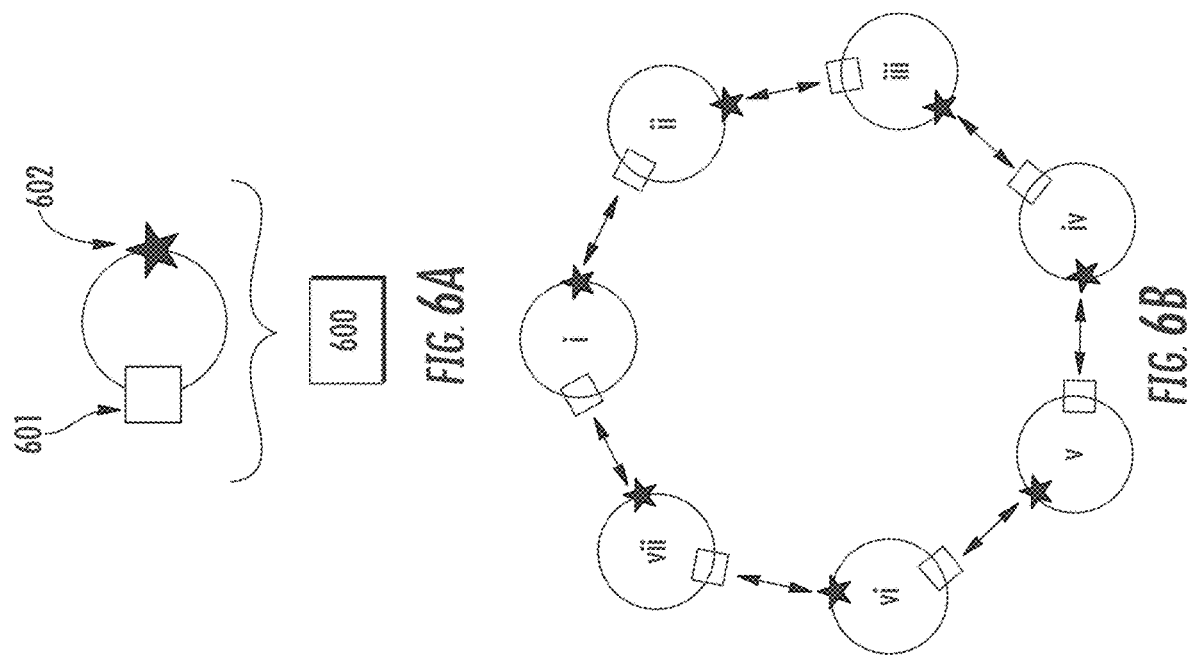
FIG. 6A
FIG. 6B

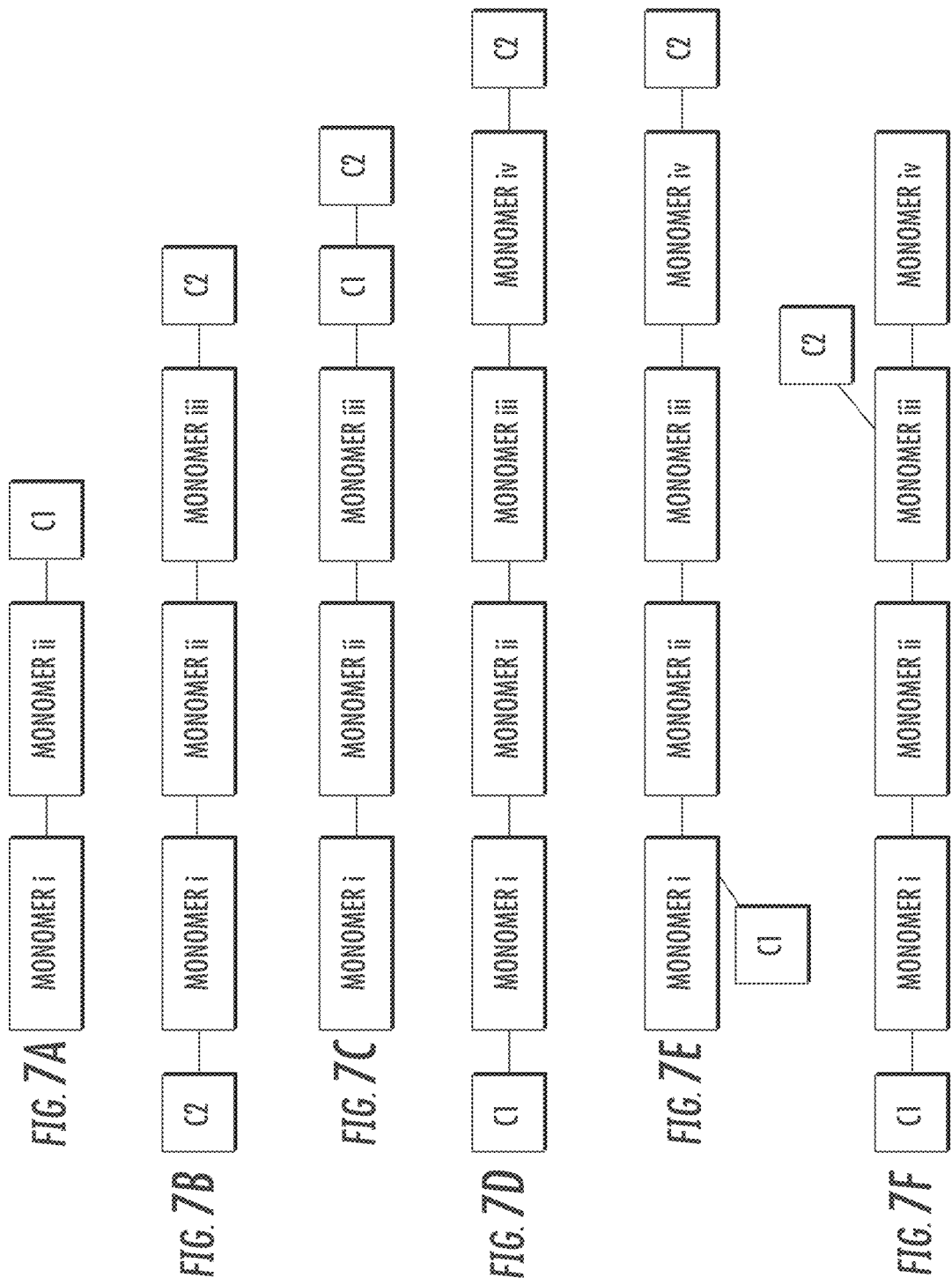

SEQUENCE LISTING

<160> NUMBER OF SEQ ID NOS: 11

<210> SEQ ID NO 1
<211> LENGTH: 1023
<212> TYPE: DNA
<213> ORGANISM: Staphylococcus aureus

<400> SEQUENCE: 1

```
atggcagatc tcgatcccgc gaaattaata cgactcacta tagggaggcc acaacggttt      60
ccctctagaa ataattttgt ttaactttaa gaaggagata tacaaatgga ttcagatatt     120
aatattaaaa caggtacaac agatattggt tcaaatacaa cagtaaaaac tggtgattta     180
gtaacttatg ataagaaaa tggtatgcat aaaaaagtat tttattcttt tattgatgat     240
aaaaatcata ataaaaaatt gttagttatt cgtacaaaag gtactattgc aggtcaatat     300
agagtatata gtgaagaagg tgctaataaa agtggtttag catggccatc tgcttttaaa     360
gttcaattac aattacctga taatgaagta gcacaaattt cagattatta tccacgtaat     420
agtattgata caaagaata tatgtcaaca ttaacttatg gttttaatgg taatgtaaca     480
ggtgatgata ctggtaaaat tggtggttta attggtgcta atgtttcaat tggtcataca     540
ttaaaatatg tacaaccaga ttttaaaaca attttagaaa gtcctactga taaaaaagtt     600
ggttggaaag taatttttaa taatatggtt aatcaaaatt ggggtcctta tgatcgtgat     660
agttggaatc ctgtatatgg taatcaatta tttatgaaaa caagaaatgg ttctatgaaa     720
gcagctgata atttcttaga tccaaataaa gcatcaagtt tattatcttc aggtttttct     780
cctgattttg caacagttat tactatggat agaaaagcat caaaacaaca aacaaatatt     840
gatgttattt atgaacgtgt aagagatgat tatcaattac attggacatc aactaattgg     900
aaaggtacaa atactaaaga taatggaca gatagaagtt cagaaagata taaaattgat     960
tgggaaaaag aagaaatgac aaatggtctc agcgcttgga gccacccgca gttcgaaaaa    1020
taa                                                                  1023
```

<210> SEQ ID NO 2
<211> LENGTH: 306
<212> TYPE: PRT
<213> ORGANISM: Staphylococcus aureus

<400> SEQUENCE: 2

```
Met Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
            20                  25                  30

Asn Gly Met His Lys Lys Val Phe Tyr Ser Phe Ile Asp Asp Lys Asn
        35                  40                  45

His Asn Lys Lys Leu Leu Val Ile Arg Thr Lys Gly Thr Ile Ala Gly
    50                  55                  60
```

Gln Tyr Arg Val Tyr Ser Glu Glu Gly Ala Asn Lys Ser Gly Leu Ala
65                  70                  75                  80

Trp Pro Ser Ala Phe Lys Val Gln Leu Gln Leu Pro Asp Asn Glu Val
                85                  90                  95

Ala Gln Ile Ser Asp Tyr Tyr Pro Arg Asn Ser Ile Asp Thr Lys Glu
            100                 105                 110

Tyr Met Ser Thr Leu Thr Tyr Gly Phe Asn Gly Asn Val Thr Gly Asp
        115                 120                 125

Asp Thr Gly Lys Ile Gly Gly Leu Ile Gly Ala Asn Val Ser Ile Gly
    130                 135                 140

His Thr Leu Lys Tyr Val Gln Pro Asp Phe Lys Thr Ile Leu Glu Ser
145                 150                 155                 160

Pro Thr Asp Lys Lys Val Gly Trp Lys Val Ile Phe Asn Asn Met Val
                165                 170                 175

Asn Gln Asn Trp Gly Pro Tyr Asp Arg Asp Ser Trp Asn Pro Val Tyr
            180                 185                 190

Gly Asn Gln Leu Phe Met Lys Thr Arg Asn Gly Ser Met Lys Ala Ala
        195                 200                 205

Asp Asn Phe Leu Asp Pro Asn Lys Ala Ser Ser Leu Leu Ser Ser Gly
    210                 215                 220

Phe Ser Pro Asp Phe Ala Thr Val Ile Thr Met Asp Arg Lys Ala Ser
225                 230                 235                 240

Lys Gln Gln Thr Asn Ile Asp Val Ile Tyr Glu Arg Val Arg Asp Asp
                245                 250                 255

Tyr Gln Leu His Trp Thr Ser Thr Asn Trp Lys Gly Thr Asn Thr Lys
            260                 265                 270

Asp Lys Trp Thr Asp Arg Ser Ser Glu Arg Tyr Lys Ile Asp Trp Glu
        275                 280                 285

Lys Glu Glu Met Thr Asn Gly Leu Ser Ala Trp Ser His Pro Gln Phe
    290                 295                 300

Glu Lys
305

<210> SEQ ID NO 3
<211> LENGTH: 305
<212> TYPE: PRT
<213> ORGANISM: Staphylococcus aureus

<400> SEQUENCE: 3

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

```
Thr Gly Lys Ile Gly Gly Leu Ile Gly Ala Asn Val Ser Ile Gly His
        130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
                180                 185                 190

Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
        210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
                260                 265                 270

Lys Trp Thr Asp Arg Ser Glu Arg Tyr Lys Ile Asp Trp Glu Lys
            275                 280                 285

Glu Glu Met Thr Asn Gly Leu Ser Ala Trp Ser His Pro Gln Phe Glu
290                 295                 300

Lys
305

<210> SEQ ID NO 4
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Asp Ser Asp Ile Asn Ile Lys Thr Gly Thr Thr Asp Ile Gly Ser
1               5                   10                  15

Lys Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
```

```
                    165                 170                 175
Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn Gly Leu Ser Ala Trp Ser His Pro Gln Phe Glu
    290                 295                 300

Lys
305

<210> SEQ ID NO 5
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ala Asp Ser Asp Ile Asn Ile Lys Thr Gly Thr Thr Asp Ile Gly Ser
1               5                   10                  15

Arg Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
            85                  90                  95

Gln Ile Ser Asp Tyr Tyr Pro Arg Asn Ser Ile Asp Thr Lys Glu Tyr
        100                 105                 110

Met Ser Thr Leu Thr Tyr Gly Phe Asn Gly Asn Val Thr Gly Asp Asp
    115                 120                 125

Thr Gly Lys Ile Gly Gly Leu Ile Gly Ala Asn Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
            165                 170                 175

Gln Asn Trp Gly Pro Tyr Asp Arg Asp Ser Trp Asn Pro Val Tyr Gly
        180                 185                 190

Asn Gln Leu Phe Met Lys Thr Arg Asn Gly Ser Met Lys Ala Ala Asp
    195                 200                 205
```

```
Asn Phe Leu Asp Pro Asn Lys Ala Ser Ser Leu Leu Ser Ser Gly Phe
        210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
        260                 265                 270

Lys Trp Thr Asp Arg Ser Ser Glu Arg Tyr Lys Ile Asp Trp Glu Lys
            275                 280                 285

Glu Glu Met Thr Asn Gly Leu Ser Ala Trp Ser His Pro Gln Phe Glu
        290                 295                 300

Lys
305

<210> SEQ ID NO 6
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Asp Ser Asp Ile Asn Ile Lys Thr Gly Thr Lys Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255
```

-continued

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
            275                 280                 285

Glu Glu Met Thr Asn Gly Leu Ser Ala Trp Ser His Pro Gln Phe Glu
            290                 295                 300

Lys
305

<210> SEQ ID NO 7
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Asp Ser Asp Ile Asn Ile Lys Thr Gly Thr Arg Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
            50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
            115                 120                 125

Thr Gly Lys Ile Gly Gly Leu Ile Gly Ala Asn Val Ser Ile Gly His
            130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
            210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
            245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
            275                 280                 285

Glu Glu Met Thr Asn Gly Leu Ser Ala Trp Ser His Pro Gln Phe Glu
            290                 295                 300

-continued

```
                290                 295                 300

Lys
305

<210> SEQ ID NO 8
<211> LENGTH: 293
<212> TYPE: PRT
<213> ORGANISM: Staphylococcus aureus

<400> SEQUENCE: 8

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 9

Gly Ser Gly Ser Gly Ser Gly Ser Gly Ser
1               5                   10

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 10

His His His His His His
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His His His His His His Gly Ser Gly Gly
1               5                   10
```

ALPHA-HEMOLYSIN VARIANTS

CROSS-REFERENCE TO RELATED APPLICATIONS

This application is a continuation of U.S. patent application Ser. No. 15/274,770, filed Sep. 23, 2016, which claims the benefit of U.S. Provisional Application No. 62/232,175, filed Sep. 24, 2015 and of U.S. Provisional Application No. 62/244,852, filed Oct. 22, 2015, each of which is incorporated herein by reference in their entireties.

SEQUENCE LISTING

A sequence listing comprising SEQ ID NOS: 1-11 is attached hereto. Each sequence provided in the sequence listing is incorporated herein by reference, in its entirety, for all purposes. Said ASCII copy, created on Jan. 2, 2019, is named 04338_544US2_Seq_Listing.txt and is 108 kilobytes in size.

TECHNICAL FIELD

Disclosed are compositions and methods relating to *Staphylococcal aureus* alpha-hemolysin variants, and αHL mutated variants. The alpha-hemolysin (α-HL) variants are useful, for example, as a nanopore in a device for determining polymer sequence information. The αHL mutated variants are useful for manipulating the stoichiometry of subunits to provide functional heptameric αHL pores. The nanopores, methods and systems described herein provide quantitative detection of single strand nucleic acids, such as DNA, RNA, etc., employing nanopore-based single-molecule technology with improved characteristics.

BACKGROUND

Hemolysins are members of a family of protein toxins that are produced by a wide variety of organisms. Some hemolysins, for example alpha hemolysins, can disrupt the integrity of a cell membrane (e.g., a host cell membrane) by forming a pore or channel in the membrane. Pores or channels that are formed in a membrane by pore forming proteins can be used to transport certain polymers (e.g., polypeptides or polynucleotides) from one side of a membrane to the other.

Alpha-hemolysin (α-HL, α-HL, αHL, αHL or alpha-HL) is a self-assembling toxin which forms an aqueous channel in the membrane of a host cell. Alpha-HL has become a principal component for the nanopore sequencing community. It has many advantageous properties including high stability, self assembly and a pore diameter which is wide enough to accommodate single stranded DNA but not double stranded DNA (Kasianowicz et al., 1996).

Previous work on DNA detection in the α-HL pore has focused on analyzing the ionic current signature as DNA translocates through the pore (Kasianowicz et al., 1996, Akeson et al., 1999, Meller et al., 2001), a very difficult task given the translocation rate (~1 nt/μs at 100 mV) and the inherent noise in the ionic current signal. Higher specificity has been achieved in nanopore-based sensors by incorporation of probe molecules permanently tethered to the interior of the pore (Howorka et al., 2001a and Howorka et al., 2001b; Movileanu et al., 2000).

The wild-type α-HL results in significant number of deletion errors, i.e., bases are not measured. Therefore, α-HL nanopores with improved properties are desired.

BRIEF SUMMARY OF THE INVENTION

The invention features a mutant staphylococcal alpha hemolysin (αHL) polypeptide containing an amino acid variation that enhances the time to thread (TTT), e.g., decreases the time to capture of the molecule of interest, e.g., relative to the TTT of the parent or wild type αHL.

The presently disclosed variants reduce the time thread of the molecule of interest, e.g., various tagged nucleotides or a nucleotide to be sequenced.

Disclosed herein are α-hemolysin (αHL) variants. The α-hemolysin (αHL) variants are derived from a parental α-HL polypeptide, e.g., SEQ ID NO:3, and comprise one or more mutation(s) relative to the parental α-HL polypeptide. In some embodiments, the variant includes a substitution at a position corresponding to position 12 or 17 of SEQ ID NO:3 (mature α-HL). In some embodiments, the variant further comprises substitution H144A. In some embodiments, the substitution comprises one or more positive charges. In some embodiments, the variant comprises a substitution at a position corresponding to one or more of residues T12 and/or N17. In some embodiments, the variant comprises a substitution selected from T12K, T12R, N17K, N17R and combinations thereof. In some embodiments, the variant has an altered time to thread (TTT) relative to the parent α-hemolysin. In some embodiments, the TTT is decreased. In some embodiments, the variant comprises a substitution at a position corresponding to a residue selected from the group consisting of T12R or T12K, and/or N17R or N17K in α-hemolysin (αHL) from *Staphylococcus aureus* (SEQ ID NOs:1 and 3). In some embodiments, the substitution is T12K. In some embodiments, the substitution is T12R. In some embodiments, the substitution is N17K. In some embodiments, the substitution is N17R. In some embodiments, the variant α-HL having an altered characteristic as compared to a parental α-hemolysin (e.g., AAA26598) comprises H144A and at least one additional mutation selected from
  a. T12K/R;
  b. N17K/R;
or combinations thereof.

In some embodiments, the amino acid substitution allows the addition of heterologous molecules, e.g., PEG. In some embodiments, the α-HL variant has post-translational modifications.

In some embodiments, the substitution is a non-native amino acid that is basic or positively charged at a pH from about 5 to about 8.5.

In an aspect, there is provided a heptameric pore assembly (e.g., nanopore assembly) comprising at least one α-hemolysin (αHL) variant as described herein. In one embodiment the invention provides a heteromeric pore assembly containing a mutant αHL polypeptide (M), e.g., a pore assembly which contains a wild type (WT) staphylococcal αHL polypeptide and a mutant αHL polypeptide in which an amino acid variant (as provided for herein) of the mutant αHL polypeptide occupies a position in a transmembrane channel of the pore structure. For example, the ratio of WT and variant αHL polypeptides is expressed by the formula $WT_{7-n}M_n$, where n is 1, 2, 3, 4, 5, 6, or 7; preferably the ratio of αHL polypeptides in the heteroheptamer is $WT_{7-n}M_n$; most preferably, the ratio is $WT_6M_1$. Homomeric pores in which each subunit of the heptamer is a mutated αHL polypeptide (i.e., where n=7) are also encompassed by the invention. Heptameric pores can be assembled from concatemer subunits of at least two linked monomers in combination with concatemer subunits of at least two linked monomers. Alternatively, heptameric pores can be assembled from a combination of concatemer subunits of at least two linked monomers and individual monomers. Thus, the ratio of WT to variant subunits in heptamers of concatemers or mixtures of concatemers and monomers will depend on the size and numbers of concatemers.

In some instances, a polymerase is associated with the nanopore (e.g., covalently linked to the nanopore) and the polymerase performs nucleotide incorporation events, i.e., retains enzymatic activity.

In an aspect, there is provided a nucleic acid encoding an α-HL variant as described herein.

In an aspect, there is provided a vector comprising a nucleic acid encoding an alpha-hemolysin variant as described herein.

In an aspect, there is provided a host cell transformed with the vector comprising a nucleic acid encoding an alpha-hemolysin variant as described herein.

In an aspect, there is provided a method of producing an alpha-hemolysin variant comprising the steps of: (a) culturing a host cell comprising a nucleic acid encoding an alpha-hemolysin variant as described herein in a suitable culture medium under suitable conditions to produce alpha-hemolysin variant; and (b) obtaining said produced alpha-hemolysin variant.

In an aspect, there is provided a method for detecting a target molecule, comprising: (a) providing a chip comprising a nanopore as described herein in a membrane that is disposed adjacent or in proximity to a sensing electrode; (b) directing a nucleic acid molecule through said nanopore, wherein said nucleic acid molecule is associated with a reporter molecule, wherein said nucleic acid molecule comprises an address region and a probe region, wherein said reporter molecule is associated with said nucleic acid molecule at said probe region, and wherein said reporter molecule is coupled to a target molecule; (c) sequencing said address region while said nucleic acid molecule is directed through said nanopore to determine a nucleic acid sequence of said address region; and (d) identifying, with the aid of a computer processor, said target molecule based upon a nucleic acid sequence of said address region determined in (c).

In one aspect, there is provided a hetero-oligomeric α-hemolysin (αHL) heptamer comprising at least one preceding and at least one following oligomerization subunits, each oligomerization subunit comprising at least one αHL monomer and/or at least one concatemer of αHL monomers having one or more mutations in a first oligomerization domain, and/or one or more mutations in a second oligomerization domain; wherein at least one of said mutations on said first and/or second domain is a breaking mutation that prevents self-oligomerization of said at least one preceding and said at least one following oligomerization subunits.

In another aspect, the hetero-oligomeric αHL heptamer described herein can further comprise at least one cognate and/or rescue mutation on the first oligomerization domain in the at least one preceding oligomerization subunit and/or at least one cognate and/or rescue mutation in the second oligomerization domain in the at least one following oligomerization subunit, wherein the at least one cognate and/or rescue mutation determines inter-subunit contact between the at least one preceding and the at least one following oligomerization subunits to specify the sequence of oligomerization subunits in the hetero-oligomeric αHL heptamer. An example of cognate mutations that can be made in oligomerization domains of preceding and following subunits that enable oligomerization of the subunits is the pair of mutations H35I and Y101H.

In some aspects, the αHL heptamer can be formed by at least one preceding oligomerization subunit that is a concatemer of αHL monomers, and at least one following subunit is at least one αHL monomer.

In other aspects, the αHL heptamer can be formed by at least one preceding oligomerization subunit and at least one following oligomerization subunit that each are concatemers of αHL monomers.

In yet other aspects, the αHL heptamer can be formed by preceding and following oligomerization subunits that are αHL monomers.

In yet another aspect, the αHL heptamer can be formed by at least one preceding oligomerization subunit that is a concatemer of αHL monomers, and at least one following subunit that is an αHL monomer.

In yet another aspect, the αHL heptamer can be formed by at least one preceding oligomerization subunit that is a αHL monomer, and at least one following subunit that is a concatemer of αHL monomers.

In some cases, the monomers and/or the concatemers of monomers of the αHL heptamer comprise one or more polypeptides of SEQ ID NO:3.

In one aspect, mutations in the first oligomerization domain of an αHL heptamer can be made at positions corresponding to amino acids 2-28, 35-42, and 43-61 of SEQ ID NO:3. Examples of mutations that can be made in the first oligomerization domain include amino acid substitutions corresponding to H35D, H35E, H35I, H35L, D24A, V26D, K37S, and D24A+V26D+K37S of SEQ ID NO:3. Mutations in the second oligomerization domain can be made at positions corresponding to amino acids 95-104, 158-164, and 228-236 of SEQ ID NO:3. Examples of mutations that can be made in the second oligomerization domain include amino acid substitutions corresponding to T233R, S99K, Y101D, Y101H, and T233R+S99K of SEQ ID NO:3.

In all aspects, the αHL heptamer retains the ability to form a pore in a lipid bilayer.

In some cases, the αHL heptamer can further comprise a polymerase that is attached to one or more of the preceding and/or following oligomerization subunits. In another aspect, in addition to the mutations in the first and/or second oligomerization domains, the αHL heptamer can further comprise an αHL polypeptide comprising an amino acid substitution at a position corresponding to position 12 or 17 of SEQ ID NO:3, wherein the substitution comprises one or more positive charges. The substitution at positions 12 or 17 can be selected from T12K, T12R, N17K, N17R and combinations thereof. αHL heptamers comprising αHL polypeptides having substitutions at positions 12 or 17 may have an altered time to thread (TTT) relative to the parent α-hemolysin. For example, the TTT can be decreased.

In another aspect, a plurality of polynucleotides encoding at least one preceding and one following oligomerization subunits of the hetero-oligomeric αHL heptamer described herein, are provided.

In another aspect, provided are host cells transformed or transfected with an expression vector encoding one of each of the polynucleotides encoding the oligomerization subunits of the hetero-oligomeric αHL heptamer.

In another aspect, a method is provided for preparing at least one preceding and at least one following oligomerization subunits of an αHL heptamer that comprises culturing the host cells transfected or transformed with polynucleotides encoding the oligomerization subunits of the hetero-oligomeric αHL heptamer. The method can further comprise isolating the at least one preceding and at least one following oligomerization subunits of the αHL heptamer from the host cell culture.

In another aspect, provided is a heptameric pore assembly comprising a hetero-oligomeric αHL heptamer as described herein.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

FIGS. 1-5 each comprise two figures, e.g., FIGS. 1A and 1B. The A figure for each figure is a histogram of the number of capture events which had a "time-to-thread" equal to the time bin shown on the x-axis. The B figure for each figure is a portion of the raw data for the corresponding figure A.

FIGS. 1A and 1B show the results for the wild-type α-hemolysin nanopore. FIG. 1A (top panel) shows "time-to-thread" data. This data is combined from many pores which were capturing the tagged nucleotides indicating the pore had both a polymerase and a template DNA molecule. The mean and median values, along with the standard deviation for wild type αHL are 20.7 ms, 16.1 ms and 1.5 ms respectively, and the total number of squarewaves used for the calculations is 41910.

FIG. 1B (bottom panel) shows some raw data with five consecutive squarewaves shown. The data points between the solid lines represent the open channel (where no tagged nucleotide is threaded in the pore) and the data in-between the dashed lines represents when the tagged nucleotide has threaded into the pore and is blocking ions moving through the channel. The electrode is cycled between positive and negative 100 mV, and in our system data points are not recorded when a negative voltage is applied. Thus, all the data points are collected from the positively applied potential, and the time where there is an absence of data points (between 1716.9-1717 sec for example) is when the electrodes have a negative voltage applied to them. In this example the "time-to-thread" measurement is calculated from squarewaves which have a threaded level observable, and, the previous squarewave had a threaded level at the end of the positive voltage (indicating that the tag was threaded in the pore and bound by the polymerase).

FIG. 2A (top panel) is data combined from many pores which were capturing the tagged nucleotides indicating the pore had both a polymerase and a template DNA molecule. The mean and median values, along with the standard deviation for T12K αHL are 19.7 ms, 14.5 ms and 1.5 ms respectively, and the total number of squarewaves used for the calculations is 4311.

FIG. 2B (bottom panel) shows some raw data with five consecutive squarewaves shown. The data points between the solid lines represent the open channel (where no tagged nucleotide is threaded in the pore) and the data in-between the dashed lines represents when the tagged nucleotide has threaded into the pore and is blocking ions moving through the channel. The electrode is cycled between positive and negative 100 mV, and in our system data points are not recorded when a negative voltage is applied. Thus, all the data points are collected from the positively applied potential, and the time where there is an absence of data points (between 1600.4-1601.2 sec for example) is when the electrodes have a negative voltage applied to them. In this example the "time-to-thread" measurement is calculated from squarewaves which have a threaded level observable, and, the previous squarewave had a threaded level at the end of the positive voltage (indicating that the tag was threaded in the pore and bound by the polymerase).

FIG. 3A is data combined from many pores which were capturing the tagged nucleotides indicating the pore had both a polymerase and a template DNA molecule. The mean and median values, along with the standard deviation for T12R αHL are 16.9 ms, 10.5 ms and 1.5 ms respectively, and the total number of squarewaves used for the calculations is 4138.

FIG. 3B (bottom panel) shows some raw data with five consecutive squarewaves shown. The data points between the solid lines represent the open channel (where no tagged nucleotide is threaded in the pore) and the data in-between the dashed lines represents when the tagged nucleotide has threaded into the pore and is blocking ions moving through the channel. The electrode is cycled between positive and negative 100 mV, and in our system data points are not recorded when a negative voltage is applied. Thus, all the data points are collected from the positively applied potential, and the time where there is an absence of data points (between 267.2-268.2 sec for example) is when the electrodes have a negative voltage applied to them. In this example the "time-to-thread" measurement is calculated from squarewaves which have a threaded level observable, and, the previous squarewave had a threaded level at the end of the positive voltage (indicating that the tag was threaded in the pore and bound by the polymerase).

FIG. 4A (top panel) is data combined from many pores which were capturing the tagged nucleotides indicating the pore had both a polymerase and a template DNA molecule. The mean and median values, along with the standard deviation for N17R αHL are 17.5 ms, 10.5 ms and 1.7 ms respectively, and the total number of squarewaves used for the calculations is 3877.

FIG. 4B (bottom panel) shows some raw data with five consecutive squarewaves shown. The data points between the solid lines represent the open channel (where no tagged nucleotide is threaded in the pore) and the data in-between the dashed lines represents when the tagged nucleotide has threaded into the pore and is blocking ions moving through the channel. The electrode is cycled between positive and negative 100 mV, and in our system data points are not recorded when a negative voltage is applied. Thus, all the data points are collected from the positively applied potential, and the time where there is an absence of data points (between 344-344.9 sec for example) is when the electrodes have a negative voltage applied to them. In this example the "time-to-thread" measurement is calculated from squarewaves which have a threaded level observable, and, the previous squarewave had a threaded level at the end of the positive voltage (indicating that the tag was threaded in the pore and bound by the polymerase).

FIG. 5A (top panel) shows combined data from many pores which were capturing the tagged nucleotides indicating the pore had both a polymerase and a template DNA molecule. The mean and median values, along with the standard deviation for N17K αHL are 5.7 ms, 2.4 ms and 0.7 ms respectively, and the total number of squarewaves used for the calculations is 2424.

FIG. 5B (bottom panel) shows some raw data with five consecutive squarewaves shown. The data points above the solid line represent the open channel (where no tagged nucleotide is threaded in the pore) and the data in-between the dashed lines represents when the tagged nucleotide has threaded into the pore and is blocking ions moving through the channel. The electrode is cycled between positive and negative 100 mV, and in our system data points are not recorded when a negative voltage is applied. Thus, all the data points are collected from the positively applied potential, and the time where there is an absence of data points (between 79.5-80.5 sec for example) is when the electrodes have a negative voltage applied to them. In this example the "time-to-thread" measurement is calculated from squarewaves which have a threaded level observable, and, the previous squarewave had a threaded level at the end of the positive voltage (indicating that the tag was threaded in the pore and bound by the polymerase).

FIG. 6A shows a diagram of an αHL subunit (600) having a first (601) oligomerization domain (□) in a first region of the subunit, and a second (602) oligomerization domain (★) in a second region of the subunit. The oligomerization subunit shown is a monomer subunit.

FIG. 6B shows a diagram of a hetero-oligomeric αHL heptamer of 7 different oligomerization subunits, which in this instance are monomers i, ii, iii, iv, v, vi, and vii. Interactions between first oligomerization domains on preceding subunits (□) and second oligomerization domains on following subunits (★) are depicted (← →).

FIG. 6C shows a diagram of subunits comprising mutations that enable inter-subunit interactions (shown as solid double arrow lines), and mutations that inhibit inter-subunit interactions (shown as crossed dashed double arrow lines). A subunit having breaking mutation 1 (BM1) does not interact with a wild type subunit (WT) or with a subunit having a breaking mutation 2 (BM2). Subunits having rescue mutations (RM) and cognate mutations (CM), can interact with a subunit having a breaking mutation, e.g., breaking mutation 1. Subunits having rescue mutations (RM) can also interact with subunits that are wild type (WT).

FIG. 6D shows a diagram of an αHL concatemer subunit of two monomers. The first oligomerization domain of the concatemer subunit (□) is present on a first subunit (shown here as vii), and the second oligomerization domain of the concatemer subunit (★) is present on a second subunit (shown here as i).

FIGS. 7A-7F show diagrams of concatemers of two (7A), three (7B, 7C) and four (7D, 7E, 7F) αHL monomers joined by linkers ( - - - ), e.g., $(GS)_5$ (SEQ ID NO: 9). Components 1 and 2 (C1, C2) can be purification components, e.g., $His_6$ (SEQ ID NO: 10), FLAG epitope, or attachment components, e.g., SpyTag.

FIGS. 8A and 8B disclose "His6-GSGG" as SEQ ID NO: 11.

DETAILED DESCRIPTION

Figure 2A:
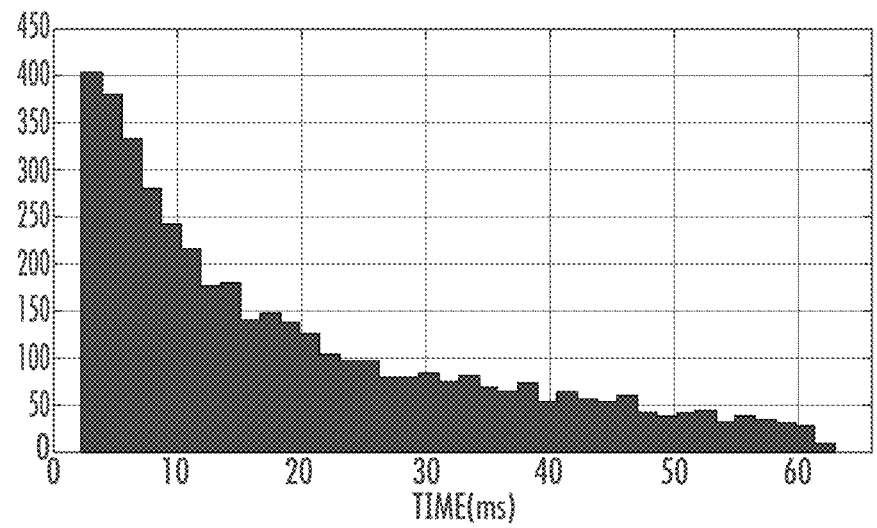
FIGS. 2A and 2B show the results for the α-hemolysin nanopore comprising a T12K mutation.
Figure 2B:
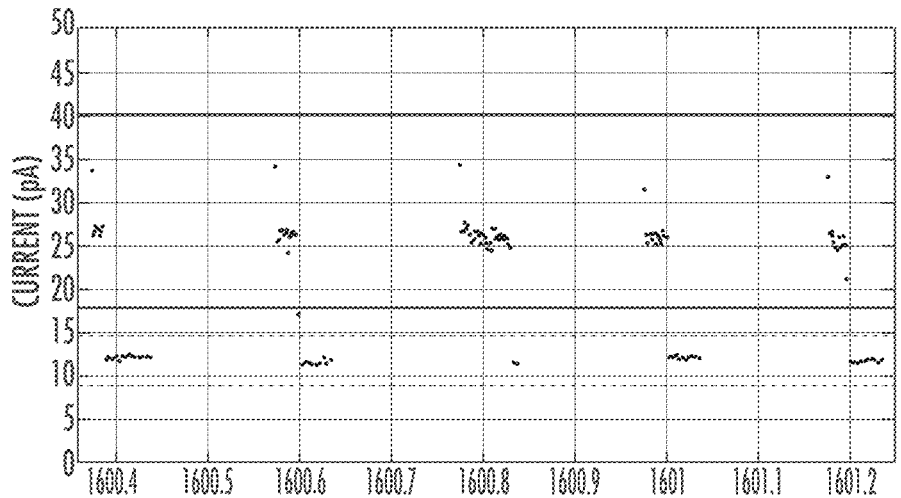
Figure 3A:
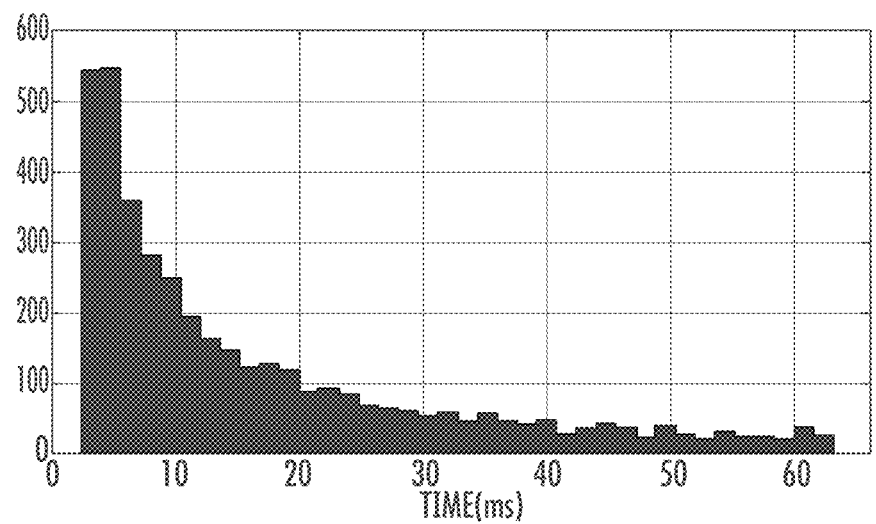
FIGS. 3A and 3B show the results for the α-hemolysin nanopore comprising a T12R mutation.
Figure 3B:
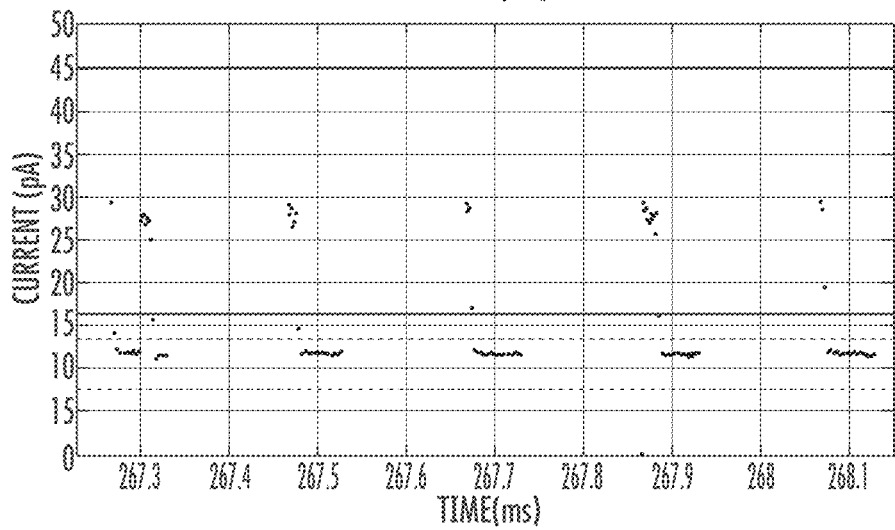
Figure 4A:
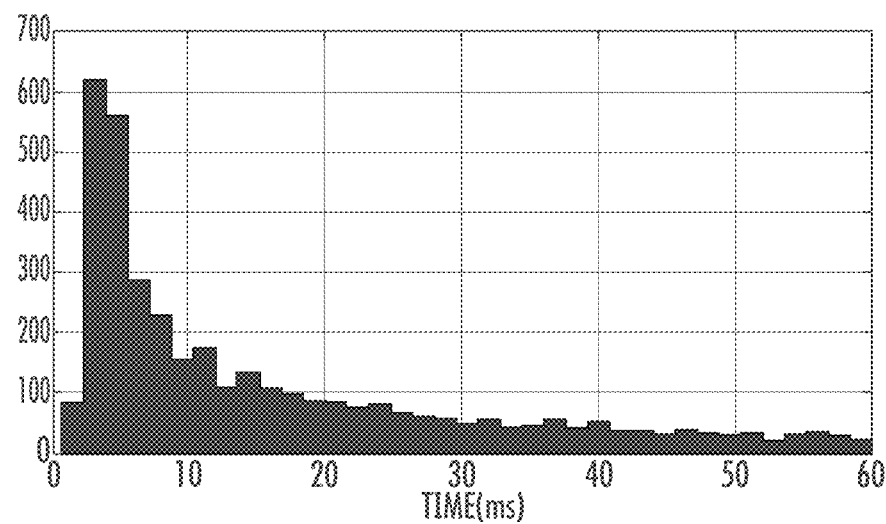
FIGS. 4A and 4B show the results for the α-hemolysin nanopore comprising a N17R mutation.
Figure 4B:
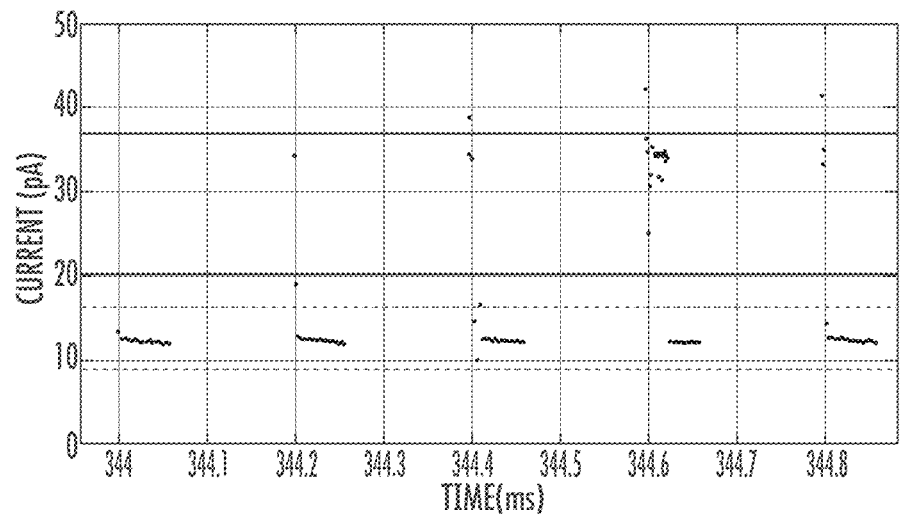
Figure 5A:
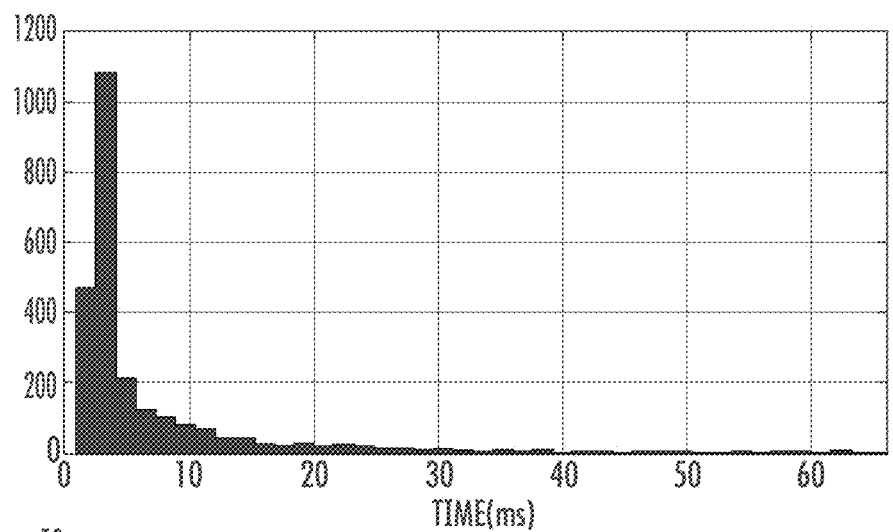
FIGS. 5A and 5B show the results for the α-hemolysin nanopore comprising a N17K mutation.
Figure 5B:
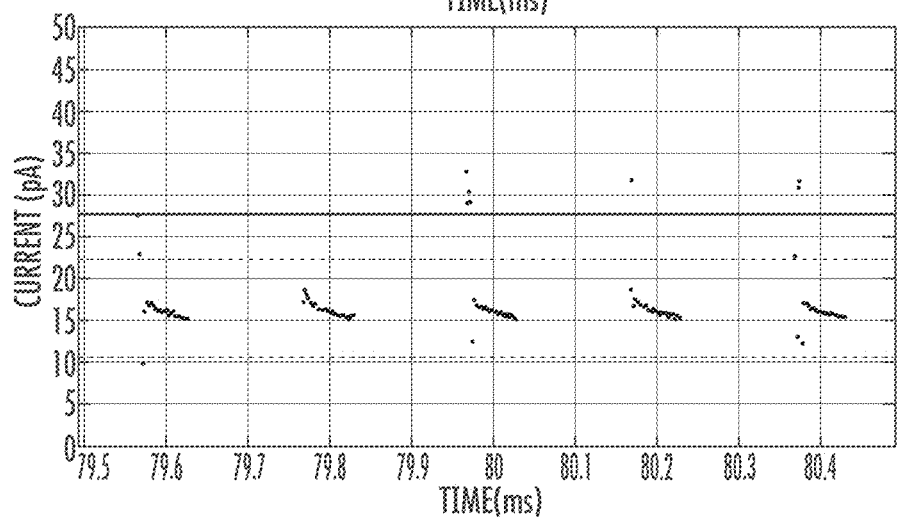

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range. The term "about" is used herein to mean plus or minus ten percent (10%) of a value. For example, "about 100" refers to any number between 90 and 110.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

Definitions

Alpha-hemolysin: As used herein, "alpha-hemolysin," "α-hemolysin," "αHL," "αHL," "α-HL" and "α-HL" are used interchangeably and refer to a protein that self-assembles into a heptameric water-filled transmembrane channel from monomers, concatemers of monomers, or a combination of monomers and concatemers of monomers.

Amino acid: As used herein, the term "amino acid," in its broadest sense, refers to any compound and/or substance that can be incorporated into a polypeptide chain. In some embodiments, an amino acid has the general structure H2N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" or "non-natural amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemicals or chemical groups without adversely affecting their activity. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide. It should be noted that all amino acid residue sequences are represented herein by formulae whose left and right orientation is in the conventional direction of amino-terminus to carboxy-terminus.

Base Pair (bp): As used herein, base pair refers to a partnership of adenine (A) with thymine (T), or of cytosine (C) with guanine (G) in a double stranded DNA molecule.

Complementary: As used herein, the term "complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

Expression cassette: An "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

Heterologous: A "heterologous" nucleic acid construct or sequence has a portion of the sequence which is not native to the cell in which it is expressed. Heterologous, with respect to a control sequence refers to a control sequence (i.e., promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

Host cell: By the term "host cell" is meant a cell that contains a vector and supports the replication, and/or transcription or transcription and translation (expression) of the expression construct. Host cells for use in the present invention can be prokaryotic cells, such as *E. coli* or *Bacillus subtilus*, or eukaryotic cells such as yeast, plant, insect, amphibian, or mammalian cells. In general, host cells are prokaryotic, e.g., *E. coli*.

Isolated: An "isolated" molecule is a nucleic acid molecule that is separated from at least one other molecule with which it is ordinarily associated, for example, in its natural environment. An isolated nucleic acid molecule includes a nucleic acid molecule contained in cells that ordinarily express the nucleic acid molecule, but the nucleic acid molecule is present extrachromasomally or at a chromosomal location that is different from its natural chromosomal location.

Modified alpha-hemolysin: As used herein, the term "modified alpha-hemolysin" refers to an alpha-hemolysin originated from another (i.e., parental) alpha-hemolysin and contains one or more amino acid alterations (e.g., amino acid substitution, deletion, and/or insertion) compared to the parental alpha-hemolysin. In some embodiments, a modified alpha-hemolysin of the invention is originated or modified from a naturally-occurring or wild-type alpha-hemolysin. In some embodiments, a modified alpha-hemolysin of the invention is originated or modified from a recombinant or engineered alpha-hemolysin including, but not limited to, chimeric alpha-hemolysin, fusion alpha-hemolysin or another modified alpha-hemolysin. Typically, a modified alpha-hemolysin has at least one changed phenotype compared to the parental alpha-hemolysin.

Mutation: As used herein, the term "mutation" refers to a change introduced into a parental sequence, including, but not limited to, substitutions, insertions, deletions (including truncations). The consequences of a mutation include, but are not limited to, the creation of a new character, property, function, phenotype or trait not found in the protein encoded by the parental sequence.

Nanopore: The term "nanopore," or "pore" as used herein, generally refers to a channel or passage formed or otherwise provided in a membrane. A membrane may be an organic membrane, such as a lipid bilayer, or a synthetic membrane, such as a membrane formed of a polymeric material. The membrane may be a polymeric material. The nanopore may be disposed adjacent or in proximity to a sensing circuit or an electrode coupled to a sensing circuit, such as, for example, a complementary metal-oxide semiconductor (CMOS) or field effect transistor (FET) circuit. In some examples, a nanopore has a characteristic width or diameter on the order of 0.1 nanometers (nm) to about 1000 nm. Some nanopores are proteins. Alpha-hemolysin is an example of a protein nanopore.

Nucleic Acid Molecule: The term "nucleic acid molecule" or "nucleic acid" or "polynucleotide" includes RNA, DNA and cDNA molecules. It will be understood that, as a result of the degeneracy of the genetic code, a multitude of nucleotide sequences encoding a given protein such as alpha-hemolysin and/or variants thereof may be produced. The present invention contemplates every possible variant nucleotide sequence, encoding variant alpha-hemolysin, all of which are possible given the degeneracy of the genetic code.

Promoter: As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

Purified: As used herein, "purified" means that a molecule is present in a sample at a concentration of at least 95% by weight, at least 98%, at least 99%, or at least 99.5% by weight of the sample in which it is contained.

Purifying: As used herein, the term "purifying" generally refers to subjecting transgenic nucleic acid or protein containing cells or extracts thereof to biochemical purification and/or column chromatography.

Tag: As used herein, the term "tag" refers to a detectable moiety that may be atoms or molecules, or a collection of atoms or molecules. A tag may provide a signature, e.g., an optical, electrochemical, magnetic, or electrostatic (e.g., inductive, capacitive) signature, which signature may be detected with the aid of a nanopore. Typically, when a nucleotide is attached to the tag it is called a "Tagged Nucleotide." The tag may be attached to the nucleotide, e.g., via the phosphate moiety.

Time-To-Thread: The term "time to thread" or "TTT" means the time it takes the polymerase-tag complex to thread the tag into the barrel of the nanopore.

Variant: As used herein, the term "variant" refers to a modified protein which displays altered characteristics when compared to the parental protein, e.g., altered ionic conductance, altered time to thread, etc.

Variant hemolysin: The term "variant hemolysin gene" or "variant hemolysin" means, respectively, that the nucleic acid sequence of the alpha-hemolysin gene from *Staphylococcus aureus* has been altered by removing, adding, and/or manipulating the coding sequence or the amino acid sequence or the expressed protein has been modified consistent with the invention described herein.

Vector: As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Wild-type: As used herein, the term "wild-type" refers to a gene or gene product which has the sequence and/or characteristics of that gene or gene product when isolated from a naturally-occurring source.

Percent homology: The term "% homology" is used interchangeably herein with the term "% identity" herein and refers to the level of nucleic acid or amino acid sequence identity between the nucleic acid sequence that encodes any one of the inventive polypeptides or the inventive polypeptide's amino acid sequence, when aligned using a sequence alignment program.

For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for any one of the inventive polypeptides, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet. See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, S. F., et al., Nucleic Acids Res. 25:3389-3402, 1997.)

A preferred alignment of selected sequences in order to determine "% identity" between two or more sequences, is performed using for example, the CLUSTAL-W program in MacVector version 13.0.7, operated with default parameters, including an open gap penalty of 10.0, an extended gap penalty of 0.1, and a BLOSUM 30 similarity matrix.

"Oligomeric proteins": The term "oligomeric proteins" herein refer to proteins that can be composed of multiple identical subunits, multiple distinct subunits, or a mixture of identical and distinct subunits. Proteins with identical subunits are termed "homo-oligomers". Proteins containing two or more distinct polypeptide subunits are termed "hetero-oligomers".

"Hetero-heptameric protein": The term "hetero-heptameric protein" herein refers to a protein containing two or more distinct subunit polypeptides, wherein each polypeptide comprises one or more αHL monomers that form a protein of seven monomers.

"Oligomerization subunit": The term "oligomerization subunit" or "subunit" herein refer to a polypeptide that comprises an amino acid sequence for at least one αHL monomer, or for at least one αHL concatemer of two, three, four, five, six, or seven monomers that are linked to each other by a linker, and are each encoded by a single polynucleotide.

"Oligomerization domain": The term "oligomerization domain" herein refers to amino acids in a region of one subunit that can interact with amino acids in a region of another subunit to enable oligomerization of the subunits. Each monomer subunit or each concatemer subunit of monomers has first and second oligomerization domains.

"Breaking mutation": The term "breaking mutation" herein refers to a mutation in an αHL subunit that does not allow for inter-subunit interaction with a wild-type αHL subunit thereby inhibiting oligomerization.

"Rescue mutation": The term "rescue mutation" herein refers to a mutation that is not a breaking mutation, which when present on the oligomerization domain of a first subunit can interface with a breaking mutation in the oligomerization domain of a second subunit to enable inter-subunit interaction thereby allowing oligomerization of the subunits. Rescue mutations can also enable oligomerization with wild type subunits. "Rescue mutations" can also be referred to as "compensating mutations".

"Cognate mutation": the term "cognate mutation" herein refers to a breaking mutation on the oligomerization domain of a first subunit that can interface with a breaking mutation in the oligomerization domain of a second subunit to enable inter-subunit interaction thereby allowing oligomerization of the subunits.

"Self-rescue mutation": the term "self-rescue mutation" herein refers to a mutation that is a breaking mutation at a first temperature (e.g., room temperature) and converts to a cognate mutation at a second temperature (e.g., 37° C.). It is understood that the first temperature may be either higher or lower than the second temperature.

"Mutated variant": The term "mutated variant" herein refers to a variant αHL subunit, e.g., monomer, that has been further modified to introduce one or more mutations, e.g., substitutions, in one or both of the oligomerization domains of an αHL subunit.

"Oligomerization mutant": the term "oligomerization mutant" herein refers to an αHL subunit having one or more mutations in one or both oligomerization domains.

Nomenclature

In the present description and claims, the conventional one-letter and three-letter codes for amino acid residues are used.

For ease of reference, variants of the application are described by use of the following nomenclature:

Original amino acid(s): position(s): substituted amino acid(s). According to this nomenclature, for instance the substitution of threonine by an arginine in position 17 is shown as:

Thr17Arg or T17R

Multiple mutations are separated by plus signs, i.e.:

Thr17Arg+Glu34Ser or T17R+E34S representing mutations in positions 17 and 34 substituting arginine and serine for threonine and glutamic acid, respectively.

When one or more alternative amino acid residues may be inserted in a given position it is indicated as: T17R/K, or T17R or T17K.

Site-Directed Mutagenesis of Alpha-Hemolysin

*Staphylococcus aureus* alpha hemolysin wild type sequences are provided herein (SEQ ID NO:1, nucleic acid coding region; SEQ ID NO:3, protein coding region) and available elsewhere (National Center for Bioinformatics or GenBank Accession Numbers M90536 and AAA26598).

Point mutations may be introduced using QuikChange Lightning 2 kit (Stategene/Agilent) following manufacturer's instructions.

Primers can be ordered from commercial companies, e.g., IDT DNA.

Nanopore Assembly and Insertion

The methods described herein can use a nanopore having a polymerase attached to the nanopore. In some cases, it is desirable to have one and only one polymerase per nanopore (e.g., so that only one nucleic acid molecule is sequenced at each nanopore). However, many nanopores, including alpha-hemolysin (αHL), can be multimeric proteins having a plurality of subunits (e.g., 7 subunits for αHL). The subunits can be identical copies of the same polypeptide. Provided herein are multimeric proteins (e.g., nanopores) having a defined ratio of modified subunits (e.g., α-HL variants) to unmodified subunits (e.g., α-HL). Also provided herein are methods for producing multimeric proteins (e.g., nanopores) having a defined ratio of modified subunits to unmodified subunits.

With reference to FIG. 27 of WO2014/074727, a method for assembling a protein having a plurality of subunits comprises providing a plurality of first subunits 2705 and providing a plurality of second subunits 2710, where the second subunits are modified when compared with the first subunits. In some cases, the first subunits are wild-type (e.g., purified from native sources or produced recombinantly). The second subunits can be modified in any suitable way. In some cases, the second subunits have a protein (e.g., a polymerase) attached (e.g., as a fusion protein).

The modified subunits can comprise a chemically reactive moiety (e.g., an azide or an alkyne group suitable for forming a linkage). In some cases, the method further comprises performing a reaction (e.g., a Click chemistry cycloaddition) to attach an entity (e.g., a polymerase) to the chemically reactive moiety.

The method can further comprise contacting the first subunits with the second subunits 2715 in a first ratio to form a plurality of proteins 2720 having the first subunits and the second subunits. For example, one part modified αHL subunits having a reactive group suitable for attaching a polymerase can be mixed with six parts wild-type αHL subunits (i.e., with the first ratio being 1:6). The plurality of proteins can have a plurality of ratios of the first subunits to the second subunits. For example, the mixed subunits can form several nanopores having a distribution of stoichiometries of modified to un-modified subunits (e.g., 1:6, 2:5, 3:4).

In some cases, the proteins are formed by simply mixing the subunits. In the case of αHL nanopores for example, a detergent (e.g., deoxycholic acid) can trigger the αHL monomer to adopt the pore conformation. The nanopores can also be formed using a lipid (e.g., 1,2-diphytanoyl-sn-glycero-3-phosphocholine (DPhPC) or 1,2-di-0-phytanyl-s/n-glycero-3-phosphocholine (DoPhPC)) and moderate temperature (e.g., less than about 100° C.). In some cases, mixing DPhPC with a buffer solution creates large multi-lamellar vesicles (LMV), and adding αHL subunits to this solution and incubating the mixture at 40° C. for 30 minutes results in pore formation.

If two different types of subunits are used (e.g., the natural wild type protein and a second αHL monomer which can contain a single point mutation), the resulting proteins can have a mixed stoichiometry (e.g., of the wild type and mutant proteins). The stoichiometry of these proteins can follow a formula which is dependent upon the ratio of the concentrations of the two proteins used in the pore forming reaction. This formula is as follows:

$$100 P_m = 100[n!/m!(n-m)!] \cdot f_{mut}^m \cdot f_{wt}^{n-m},$$

where $P_m$=probability of a pore having m number of mutant subunits n=total number of subunits (e.g., 7 for αHL)

m=number of "mutant" subunits $f_{mut}$=fraction or ratio of mutant subunits mixed together $f_{wt}$=fraction or ratio of wild-type subunits mixed together The method can further comprise fractionating the plurality of proteins to enrich proteins that have a second ratio of the first subunits to the second subunits 2725. For example, nanopore proteins can be isolated that have one and only one modified subunit (e.g., a second ratio of 1:6). However, any second ratio is suitable. A distribution of second ratios can also be fractionated such as enriching proteins that have either one or two modified subunits. The total number of subunits forming the protein is not always 7 (e.g., a different nanopore can be used or an alpha-hemolysin nanopore can form having six subunits) as depicted in FIG. 27 of WO2014/074727. In some cases, proteins having only one modified subunit are enriched. In such cases, the second ratio is 1 second subunit per (n−1) first subunits where n is the number of subunits comprising the protein.

The first ratio can be the same as the second ratio, however this is not required. In some cases, proteins having mutated monomers can form less efficiently than those not having mutated subunits. If this is the case, the first ratio can be greater than the second ratio (e.g., if a second ratio of 1 mutated to 6 non-mutated subunits are desired in a nanopore, forming a suitable number of 1:6 proteins may require mixing the subunits at a ratio greater than 1:6). Conversely, if mutated monomers are able to oligomerize more efficiently, then the first ratio can be less than the second ratio (e.g., if a second ratio of 1 mutated to 6 non-mutated monomers are desired in a nanopore, forming a suitable number of 1:6 proteins may require mixing the subunits at a ratio less than 1:6).

Proteins having different second ratios of subunits can behave differently (e.g., have different retention times) in a separation. In some cases, the proteins are fractionated using chromatography, such as ion exchange chromatography or affinity chromatography. Since the first and second subunits can be identical apart from the modification, the number of modifications on the protein can serve as a basis for separation. In some cases, either the first or second subunits have a purification tag (e.g., in addition to the modification) to allow or improve the efficiency of the fractionation. In some cases, a poly-histidine tag (His-tag), a streptavidin tag (Strep-tag), or other peptide tag is used. In some instances, the first and second subunits each comprise different tags and the fractionation step fractionates on the basis of each tag. In the case of a His-tag, a charge is created on the tag at low pH (Histidine residues become positively charged below the pKa of the side chain). With a significant difference in charge on one of the αHL molecules compared to the others, ion exchange chromatography can be used to separate the oligomers which have 0, 1, 2, 3, 4, 5, 6, or 7 of the "charge-tagged" αHL subunits. In principle, this charge tag can be a string of any amino acids which carry a charge, e.g., a uniform charge. FIG. 28 and FIG. 29 of WO2014/074727 show examples of fractionation of nanopores based on a His-tag. FIG. 28 shows a plot of ultraviolet absorbance at 280 nanometers, ultraviolet absorbance at 260 nanometers, and conductivity. The peaks correspond to nanopores with various ratios of modified and unmodified subunits. FIG. 29 of WO2014/074727 shows fractionation of αHL nanopores and mutants thereof using both His-tag and Strep-tags.

In some cases, an entity (e.g., a polymerase) is attached to the protein following fractionation. The protein can be a nanopore and the entity can be a polymerase. In some instances, the method further comprises inserting the proteins having the second ratio subunits into a bilayer.

In some situations, a nanopore can comprise a plurality of subunits. A polymerase can be attached to one of the subunits and at least one and less than all of the subunits comprise a first purification tag. In some examples, the nanopore is alpha-hemolysin or a variant thereof. In some instances, all of the subunits comprise a first purification tag or a second purification tag. The first purification tag can be a poly-histidine tag (e.g., on the subunit having the polymerase attached).

Polymerase Attached to Nanopore

In some cases, a polymerase (e.g., DNA polymerase) is attached to and/or is located in proximity to the nanopore. The polymerase can be attached to the nanopore before or after the nanopore is incorporated into the membrane. In some instances, the nanopore and polymerase are a fusion protein (i.e., single polypeptide chain).

The polymerase can be attached to the nanopore in any suitable way. In some cases, the polymerase is attached to the nanopore (e.g., hemolysin) protein monomer and then the full nanopore heptamer is assembled (e.g., in a ratio of one monomer with an attached polymerase to 6 nanopore (e.g., hemolysin) monomers without an attached polymerase). The nanopore heptamer can then be inserted into the membrane.

Another method for attaching a polymerase to a nanopore involves attaching a linker molecule to a hemolysin monomer or mutating a hemolysin monomer to have an attachment site and then assembling the full nanopore heptamer (e.g., at a ratio of one monomer with linker and/or attachment site to 6 hemolysin monomers with no linker and/or attachment site). A polymerase can also be attached to a concatemer of αHL monomers. For example, FIGS. 7A-7F show that concatemers of two or more αHL monomers can comprise attachment components to which an enzyme, e.g., a polymerase, can be linked. Accordingly, a polymerase can be linked to a concatemer of two or more monomers, which can be oligomerized with other concatemers and/or monomers to provide a nanopore, e.g., a heptameric αHL nanopore, comprising a polymerase enzyme. A second polymerase can also be linked to a monomer or to a concatemer of monomers. A polymerase can then be attached to the attachment site or attachment linker (e.g., in bulk, before inserting into the membrane). The polymerase can also be attached to the attachment site or attachment linker after the (e.g., heptamer) nanopore is formed in the membrane. In some cases, a plurality of nanopore-polymerase pairs is inserted into a plurality of membranes (e.g., disposed over the wells and/or electrodes) of the biochip. In some instances, the attachment of the polymerase to the nanopore complex occurs on the biochip above each electrode.

The polymerase can be attached to the nanopore with any suitable chemistry (e.g., covalent bond and/or linker). In some cases, the polymerase is attached to the nanopore with molecular staples. In some instances, molecular staples comprise three amino acid sequences (denoted linkers A, B and C). Linker A can extend from a hemolysin monomer, Linker B can extend from the polymerase, and Linker C then can bind Linkers A and B (e.g., by wrapping around both Linkers A and B) and thus the polymerase to the nanopore. Linker C can also be constructed to be part of Linker A or Linker B, thus reducing the number of linker molecules.

In some instances, the polymerase is linked to the nanopore using Solulink™ chemistry. Solulink™ can be a reaction between HyNic (6-hydrazino-nicotinic acid, an aromatic hydrazine) and 4FB (4-formylbenzoate, an aromatic aldehyde). In some instances, the polymerase is linked to the nanopore using Click chemistry (available from LifeTechnologies for example). In some cases, zinc finger mutations are introduced into the hemolysin molecule and then a molecule is used (e.g., a DNA intermediate molecule) to link the polymerase to the zinc finger sites on the hemolysin.

Stoichiometry and Arrangement of αHL Subunits into Heptameric Pores

In another aspect, hetero-oligomeric αHL heptamers and methods for preparing the heptamers are provided. The hetero-oligomeric heptamers can be formed by regulating the stoichiometry and the sequential arrangement of their subunit components. The sequential arrangement is determined by the interaction of mutations in oligomerization domains of the subunits.

Heptameric wild-type αHL pores are formed by self-assembly of seven wild-type monomer subunits. Each monomer subunit comprises a first and a second oligomerization domain whereby the first oligomerization domain of one subunit interacts with the second oligomerization domain of another subunit to enable the self-assembly of monomeric subunits into a heptameric αHL pore. The first oligomerization domain region, i.e., site 1 of each monomer subunit, comprises amino acids corresponding to amino acid positions 20-28, 35-42, and 53-61 of αHL of SEQ ID NO:3. The second interface region, i.e., site 2 of each αHL monomer, comprises amino acids corresponding to amino acid positions 158-164, 95-104, 43 to 48, and 228 to 236 of the αHL subunit of SEQ ID NO:3. FIG. 6A illustrates the positioning of the first (601) and second (602) oligomerization domain, respectively, of a monomer subunit. The positioning of the interaction of the oligomerization domains of the seven monomer subunits numbered i, ii, iii, iv, v, vi, and vii as they are oligomerized into a heptameric αHL pore is shown schematically in FIG. 6B.

However, assembly of engineered monomers can give rise to oligomers having undesirable stoichiometries. For example, assembly of engineered subunits can give rise to octamers consisting of four dimer subunits, or to hexamers of three dimer subunits (Hammerstein et al., 2011). Therefore, it would be advantageous to control the assembly of the αHL subunits to provide the heptameric form, which is the stoichiometry that enables the sensing capability of an αHL pore.

In one embodiment, the oligomerization of αHL subunits into a heptameric pore can be obtained by introducing mutations at interfaces, i.e., oligomerization domains, on each of the subunits to disrupt the subunit-subunit interaction. As described above, and depicted in FIGS. 6A and 6B, there are two oligomerization domains on each subunit, and one or more mutations can be introduced in the first and/or the second oligomerization domain of each subunit to inhibit inter-subunit contact and thereby prevent oligomerization of subunits into αHL multimers having undesirable subunit stoichiometries. Mutations that inhibit inter-subunit interactions are herein referred to as breaking mutations. Each oligomerization domain of each subunit can be modified to comprise one or more breaking mutations. In some embodiments, one or more amino acids in the first oligomerization domain can be mutated to provide one or more breaking mutations. Similarly, one or more amino acids in the second oligomerization domain can be mutated to provided one or more breaking mutations. In other embodiments, one or more amino acids in the first and in the second oligomerization domain of each subunit can be mutated to provide one or more breaking mutation.

Mutations that can be made at oligomerization domains include substitutions, deletions, and insertions. Preferred mutations of amino acids in these domains are amino acid substitutions.

In some embodiments, one or more of the amino acids corresponding to positions 20-28, 35-42, and 53-61 of the first oligomerization domain of the αHL subunit of SEQ ID NO:3 are mutated to introduce one or more breaking mutations into the first oligomerization domain of an αHL subunit. In some embodiments, breaking mutations at the first oligomerization domain include D24A, V26D, K37S, H35I, H35D, H35E, H35L and D24A+V26D+K37S of SEQ ID NO:3.

Figure 8A:
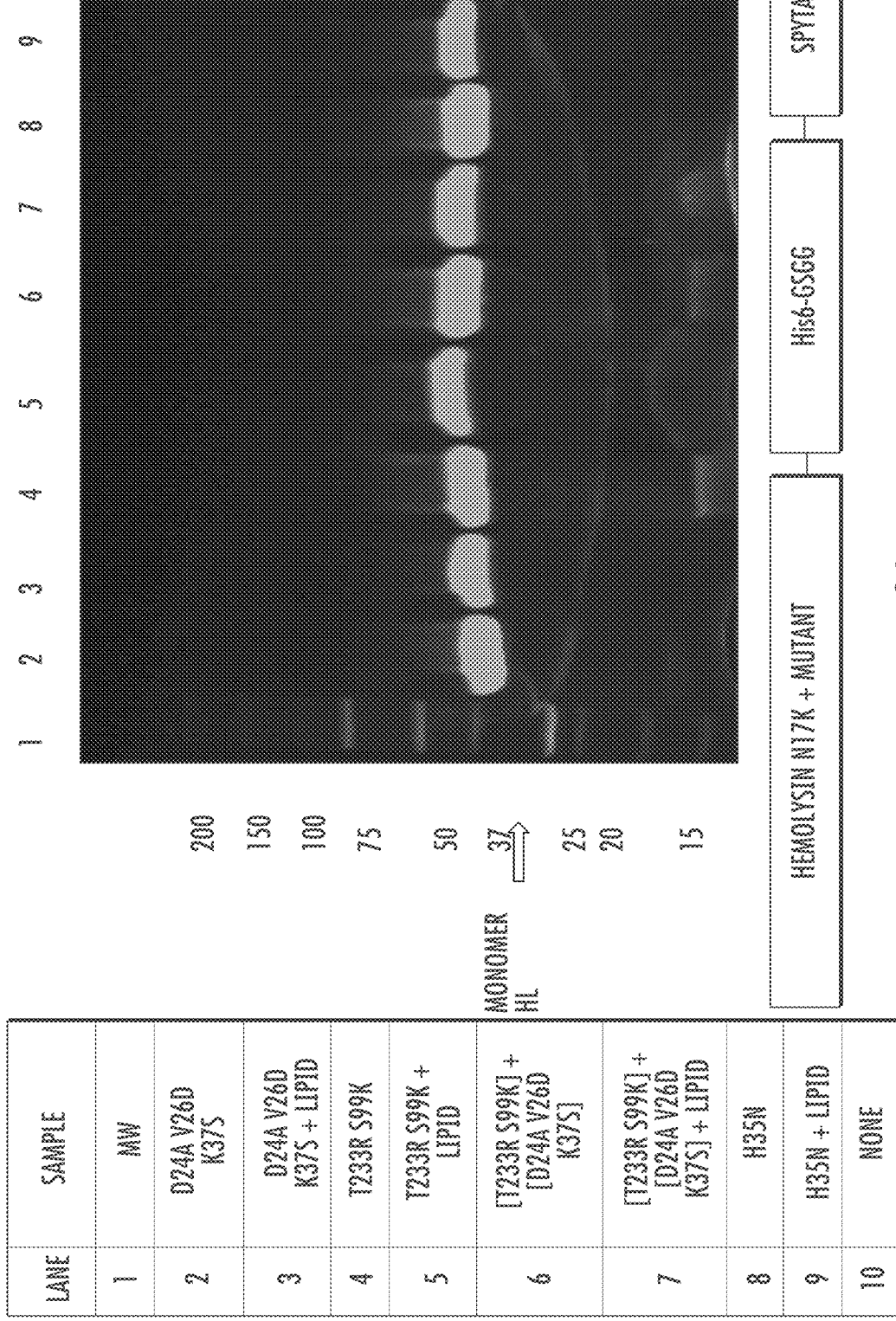
FIGS. 8A and 8B show SDS-PAGE gels demonstrating the loss of oligomerization of variant monomers (N17K) having breaking mutations at oligomerization domains as indicated. Reference is made to Example 6.
Figure 8B:
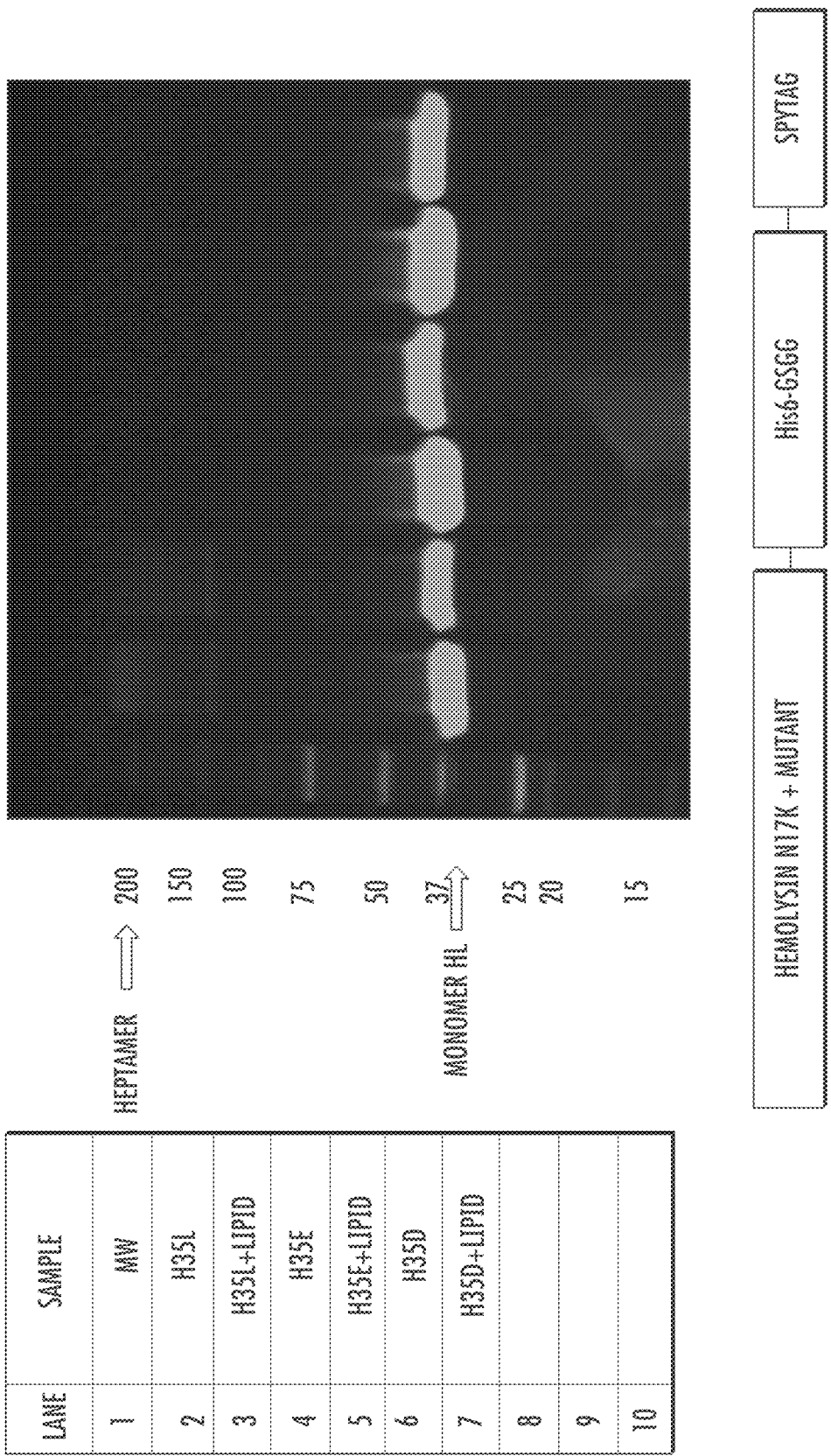

In other embodiments, one or more of the amino acids corresponding to positions 158-164, 95-104, 43 to 48, and 228 to 236 of the αHL subunit of SEQ ID NO:3 are mutated to introduce one or more breaking mutations into the second oligomerization domain of an αHL subunit. In some embodiments, breaking mutations at the second oligomerization domain include T233R, S99K, Y101 D, Y101H, and T233R+S99K of SEQ ID NO:3. FIGS. 8A and 8B show that in the presence of lipid, mutated monomers having breaking mutations at the first and/or second oligomerization domains cannot be reconstituted into an oligomeric protein.

To enable controlled oligomerization of subunits comprising breaking mutations, rescue and/or cognate mutations are introduced in one or both of the oligomerization domains of subunits to revert the effect of the breaking mutations and allow for the requisite inter-subunit interaction that is necessary for oligomerization and formation of the heptameric nanopore. FIG. 6C shows the types of interactions between mutations on oligomerization domains of αHL subunits that allow or inhibit oligomerization. Breaking mutations 1 and 2 (BM1, BM2) inhibit oligomerization of the subunits via the domains in which they reside. Similarly, a breaking mutation, e.g., BM1, inhibits oligomerization with a wild-type subunit. Inhibition of oligomerization is shown by the crossed broken arrow lines. Reversal of the breaking effect of breaking mutations, e.g., BM1, is enabled by cognate mutations (CM) and/or rescue mutations (RM). Enablement of oligomerization is depicted by the solid arrow lines.

Cognate mutations (CM), which are themselves breaking mutations, when present on the oligomerization domain of a first subunit, can interact with breaking mutations (e.g., BM1) on the oligomerization domain of another subunit to restore the ability of the two subunits to oligomerize. The pairing of the breaking and cognate mutations also specifies which two subunits can interact in the process. In some embodiments, a breaking mutation on a first oligomerization domain of one subunit, i.e., a preceding subunit, allows for the interaction of a second subunit via a cognate mutation on a second oligomerization domain on a second subunit, i.e., a following subunit, as the cognate mutation reverts the effect of the breaking mutation to allow inter-subunit interaction via the first and second domains.

Rescue mutations (RM), which are not breaking mutations, when present on the oligomerization domain of a first subunit, can interact with breaking mutations (e.g., BM1) on the oligomerization domain of another subunit to restore the ability of the two subunits to oligomerize. The pairing of the breaking and rescue mutations also specifies which two subunits can interact in the process. In some embodiments, a breaking mutation on a first oligomerization domain of one subunit, i.e., a preceding subunit, allows for the interaction of a second subunit via a rescue mutation on a second oligomerization domain on a second subunit, i.e., a following subunit, as the rescue mutation reverts the effect of the breaking mutation to allow inter-subunit interaction via the first and second domains.

Thus, in some embodiments, at least one of the mutations of the one or more of the amino acids corresponding to positions 20-28, 35-42, and 53-61 of the first oligomerization domain of the αHL subunit of SEQ ID NO:3 is a breaking mutation, and/or at least one of the mutations of the one or more of the amino acids corresponding to positions 158-164, 95-104, 43 to 48, and 228 to 236 of the second oligomerization domain of the αHL subunit of SEQ ID NO:3 is a rescue and/or cognate mutation that enables inter-subunit interaction with corresponding second and first oligomerization domains of following or preceding subunits, respectively. Alternatively, at least one of the mutations of the one or more of the amino acids corresponding to positions 158-164, 95-104, 43 to 48, and 228 to 236 of the second oligomerization domain of SEQ ID NO:3 is a breaking mutation, and/or at least one of the mutations one or more of the amino acids corresponding to positions 20-28, 35-42, and 53-61 of the first oligomerization domain αHL subunit of SEQ ID NO:3 is a cognate and/or rescue mutation. It is understood that breaking mutations in one domain of one subunit can interact with rescue and/or cognate mutations of a domain of another subunit to enable oligomerization of the subunits. The one or more breaking mutations inhibit oligomerization of the subunit by at least about 10%, 20%, 30% 40%, 50%, 60%, 70%, 80%, 85%, 90%, 95%, or more when compared to the oligomerization of the unmutated αHL subunits. The one or more rescue and/or cognate mutations on one subunit enable inter-subunit interaction with breaking mutations on another subunit to obtain at least about 10%, 20%, 30% 40%, 50%, 60%, 70%, 80%, 85%, 90%, 95%, or more oligomerization of the subunits when compared to the oligomerization of the unmutated αHL subunits or when compared to the oligomerization of the subunit without the rescue and/or cognate mutation with the subunit that comprises the breaking mutation.

In another embodiment, inter-subunit interaction can be established between a breaking mutation in a first oligomerization domain on a preceding subunit and a rescue mutation and/or a cognate mutation in the second domain of a following subunit. Accordingly, at least one breaking mutation can be made in each of the first oligomerization domain of a preceding subunit and at least one breaking mutation can be made in each of the second oligomerization domain of a following subunit. In some embodiments, at least one of the breaking mutations in the second oligomerization domain of a following subunit is a cognate mutation that when paired with a breaking mutation on the preceding subunit allows for inter-subunit interaction, thereby enabling oligomerization of the subunits. In other embodiments, the mutation in the second oligomerization domain of a following subunit is a rescue mutation that when paired with a breaking mutation on the first oligomerization domain of a preceding subunit, allows for inter-subunit interaction, thereby enabling oligomerization of the subunits.

Figure 14:
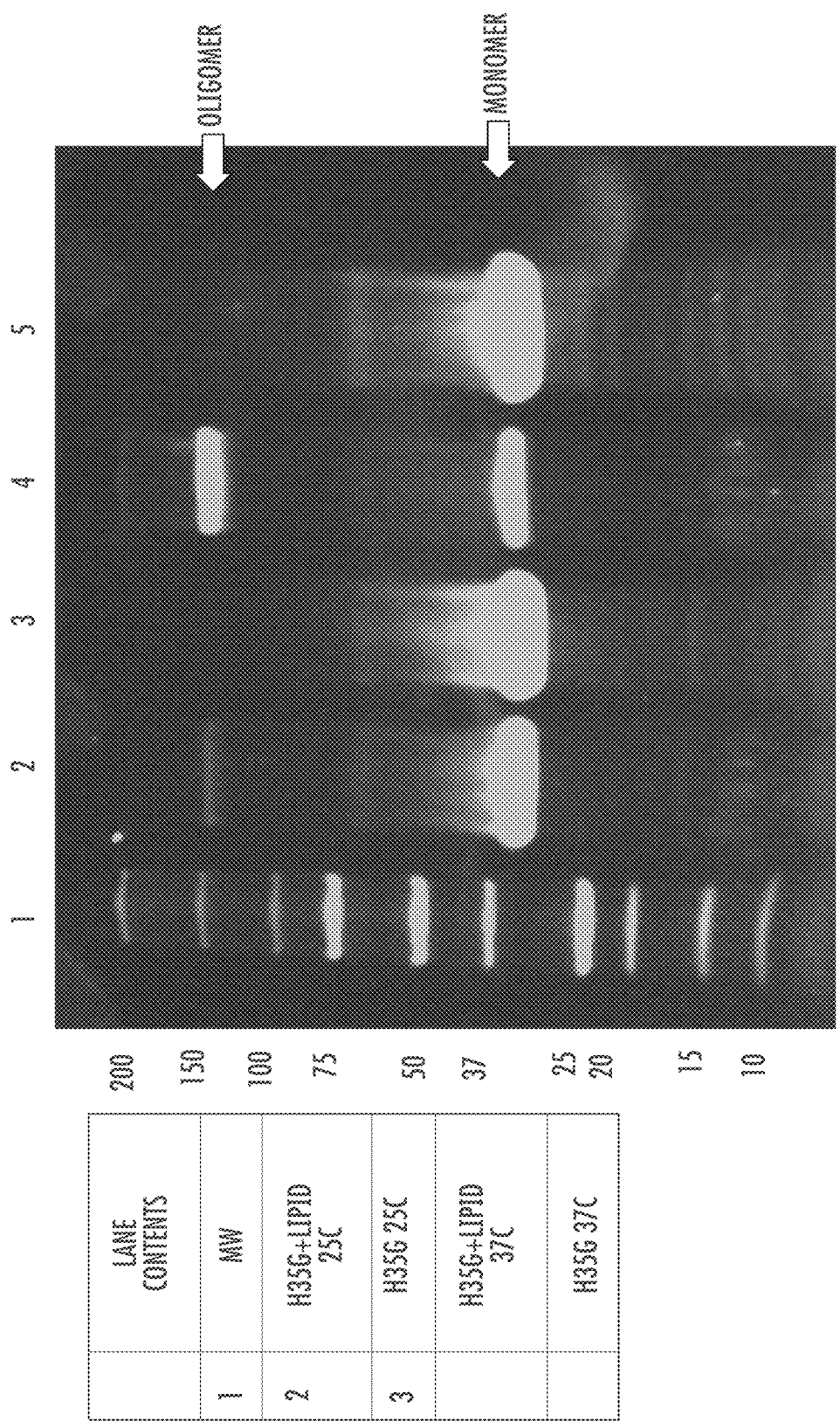
FIG. 14 shows an image of an SDS-PAGE gel that demonstrates the temperature-dependent oligomerization of monomers that have the H35G mutation. Reference is made to Example 11.

In some embodiments, oligomerization subunits can comprise at least one breaking mutation that can convert itself to a cognate mutation, i.e., the breaking mutation can be a self-rescue mutation. Applicants discovered that there exist breaking mutations that inhibit oligomerization of monomers at temperatures below 30° C., but which enable oligomerization when the process is performed at temperatures greater than 30° C. For example, and in reference to Example 11 and FIG. 14, monomers having a breaking mutation H35G of SEQ ID NO:3, are unable to oligomerize at 25° C. However, when reconstitution of the same monomers, i.e., monomers having the same H35G mutation, the monomers are able to oligomerize at 37° C. Accordingly, in some embodiments, heptamers can comprise at least one breaking mutation in the first and/or second oligomerization domain that is a self-rescue mutation, which enables oligomerization of subunits. In some embodiments, conversion of breaking mutations to self-rescue mutation takes place at temperatures between 30° C. and 50° C., between 35° C. and 45° C., or between 37° C. and 43° C. In some embodiments, conversion of breaking mutations to self-rescue mutation takes place at any of about 30° C., 35° C., 40° C., 45° C., or 50° C. It is understood that absent denaturation, conversion of breaking mutations to self-rescue mutation can take place at temperatures greater than 50° C. In some embodiments, the self-rescue mutation is the amino acid substitution corresponding to H35G in SEQ ID NO:3.

Self-rescue mutations are particularly useful as it is advantageous to oligomerize pore subunits, e.g., monomers, at higher temperatures. Protein expression at lower temperatures of variants comprising self-rescue mutations allows for accurate determination of monomer concentration due to the inhibition/blockade of oligomerization. In contrast, wild-type monomers can oligomerize and exist as a mixture of monomers and oligomers. The WT oligomerization leads to inaccurate measurements of monomer concentration. Knowledge of the true concentration of monomers in a solution is critical in obtaining the correct ratio of subunit types needed to create the desired heptameric pore. Accordingly, a self-rescue mutation, which behaves as a breaking mutation at lower temperatures prevents oligomerization and thereby allows for accurate determination of monomer concentration. Subsequently, the desired heptameric pore can be obtained at higher temperatures at which the same breaking mutation converts to a self-rescue mutation to allow for the desired oligomerization.

Oligomerization subunits can be monomers, or they can be concatemers of two linked monomers (dimer concatemer), three linked monomers (trimer concatemer), four linked monomers (tetramer concatemer), five linked monomers (penta-concatemers), six linked monomers (hexa-concatemers), and seven linked monomers (hepta-concatemers). The first oligomerization domain of a concatemer subunit is the first oligomerization domain of the first monomer of the concatemer (N-terminal); and the second oligomerization domain of the concatemer subunit is the second oligomerization domain of the last (C-terminal) monomer of the concatemer. The monomer subunits can be linked by linker polypeptides that join the C-terminal end of a preceding monomer to the N-terminal end of a following monomer. FIG. 6D shows an oligomerization subunit that is a concatemer of two αHL monomers vii and i, which are joined by a linker (------). In this concatemer subunit, the first oligomerization domain (□) is the first oligomerization domain of the first subunit vii, and the second oligomerization domain of the concatemer subunit (★) is the second oligomerization domain of the second αHL monomer in the concatemer (i). The linker can be any form of molecule that links the first and second regions by covalent forces. In particular, the linker can be a peptide or polypeptide of any length that will function in the context of the invention, including any of about 1, 2, 3, 4, 5, 6, 7, 8, 9, 10, 15, 20, 25, 30, 40, 50, or more amino acids, or any number or range of amino acids that will work for the purposes of the invention. The amino acid linker can include synthetic or naturally occurring amino acid residues. Those of ordinary skill in the art will be able to determine and test any number of types and lengths of linkers. The linker can be between the C-terminus of the preceding subunit and the N-terminus of the following subunit. In some embodiments, the linker is a flexible linker of up to 5, up to 10, up to 15, up to 20, up to 25, or up to 30 amino acids. In some embodiments the linker is of about 10 amino acids. In other embodiments, the linker is of about 5 amino acids.

In some embodiments, an attachment component and/or a purification component can be provided at one or both the C-terminus and N-terminus of the concatemer polypeptide. Purification components include but are not limited to His6 (SEQ ID NO: 10) and FLAG epitopes. Attachment components include but are not limited to the SpyTag/SpyCatcher peptide system (Zakeri et al. PNAS 109:E690-E697 [2012]), native chemical ligation (Thapa et al., Molecules 19:14461-14483 [2014]), sortase system_(Wu and Guo, J Carbohydr Chem 31:48-66 [2012]; Heck et al., Appl Microbiol Biotechnol 97:461-475 [2013])), transglutaminase systems (Dennler et al., Bioconjug Chem 25:569-578 [2014]), formylglycine linkage (Rashidian et al., Bioconjug Chem 24:1277-1294 [2013]), or other chemical ligation techniques known in the art. Attachment components can serve to attach an enzyme, e.g., a polymerase, to the αHL subunit. Enzymes that can be attached to an αHL pore include polymerases, e.g., DNA polymerases, RNA polymerases, and reverse transcriptases. In some embodiments, a polymerase can be attached to two different αHL subunits within an αHL heptameric pore by attachment components on two different αHL subunits. In other embodiments, a polymerase can be attached to three different αHL subunits of an αHL heptameric pore by attachment components on three different αHL subunits. In other embodiments, two or more enzymes may be attached to any number of αHL subunits. FIGS. 7A-7F also show examples of concatemer subunits of two, three, and four monomers and the positioning of attachment and/or purification components.

The mutated monomers or concatemers of monomers comprising the one or more mutations in the first and second oligomerization domains can further comprise one or more mutations in regions other than the first and second oligomerization domain of the polypeptide monomer or monomer concatemer. For example, the variant αHL monomer polypeptide that comprises an amino acid substitution at a position corresponding to position 12 or 17 of SEQ ID NO:3, which alters the TTT of the αHL relative to that of a parent αHL, can be further mutated to comprise mutations, e.g., amino acid substitutions at first and second oligomerization domains to confer the ability of the subunits to form a heptameric αHL pore.

Further embodiments relate to nucleic acids that encode the mutated αHL oligomerization subunits of monomers and of concatemers of monomers. These nucleic acids, in some embodiments, encode oligomerization subunits having one or more mutations at a first oligomerization domain and/or at a second oligomerization domain as described elsewhere herein. In some embodiments, the starting ATG of a monomer that is linked to the C-terminus of a preceding monomer in a concatemer subunit is removed to avoid late initiation products.

The polynucleotides can further comprise a signal sequence.

In some embodiments, the polynucleotides further comprise sequence(s) that encode linkers that join monomer units in concatemers of monomers, as described elsewhere herein.

In other embodiments, the polynucleotides comprise sequence(s) that encode purification and/or attachment components.

In some embodiments, the polynucleotides comprise sequence(s) that encode a purification component and/or an attachment component (FIGS. 7A-7F). The purification and/or attachment components can be positioned at the N-terminus and/or C-terminus of the oligomerization subunit. Purification and/or attachment components can also be attached at any region within the polypeptide, i.e., at a region that is between the C-terminus and the N-terminus. In some embodiments, the purification and attachment components can be positioned at the N-terminus or C-terminus of the oligomerization subunit. In some embodiments, at least one purification component can be positioned at the N-terminus and the attachment component can be positioned at the C-terminus of the oligomerization subunit. In other embodiments, at least one purification component can be positioned at the C-terminus and the attachment component can be positioned at the N-terminus of the oligomerization subunit. In some embodiments, at least one attachment component can be positioned within the polypeptide and the purification component can be positioned at the C-terminus. In some embodiments, at least one attachment component can be positioned within the polypeptide and the purification component can be positioned at the N-terminus.

In some aspects of the invention, the nucleic acids are expressible to produce polypeptides. The polypeptides may be expressed in prokaryotic cells or eukaryotic cells or expressed in a cell free system. Preferred cells for expression include, but are not limited to, bacterial cells, insect cells, yeast cells, and mammalian cells.

Another aspect of the current invention comprises vectors that comprise a nucleic acid encoding all or part of a polypeptide of the present invention. The vectors may, for example, be cloning or expression vectors. The cloning vectors of the invention may be comprised in any suitable recombinant host cell, as described elsewhere herein or known to those of skill in the art.

Methods for preparing hetero-oligomeric αHL heptamer proteins are also provided. A polynucleotide encoding a mutated αHL subunit is expressed in a host cell. Different polynucleotides encoding different mutated αHL subunits are expressed individually in different host cells. Optionally, each of the expressed subunit polypeptides is purified, and subsequently mixed to allow for oligomerization into a hetero-oligomeric αHL heptamer. In some embodiments, the method can comprise providing a first polynucleotide encoding a first mutated αHL subunit having one or more breaking mutations in the first oligomerization domain and/or in the second oligomerization domain, culturing a host cell transformed or transfected with an expression vector encoding the first polynucleotide encoding the first mutated αHL subunit; providing a second polynucleotide encoding a second mutated αHL subunit having at least one rescue and/or cognate mutation in a first and/or second oligomerization domain, culturing a second host cell transformed or transfected with an expression vector encoding the second polynucleotide encoding the second αHL subunit, wherein the first and second mutated αHL subunits oligomerize to form at least an αHL dimer, at least an αHL trimer, at least an HL tetramer, at least an αHL pentamer, at least an αHL hexamer, or at least an αHL heptamer. The method can further comprise purifying the first and a second mutated αHL subunits. Purified αHL subunits can be oligomerized in the presence of lipid to form heptameric αHL pores. It is understood that heptameric αHL pores can be formed by oligomerization of single monomer subunits, e.g., seven αHL monomer subunits, by oligomerization of concatemer subunits, e.g., a concatemer of three αHL monomers and a concatemer of four αHL monomers, or by oligomerization of a mixture of αHL monomer subunits, and αHL concatemer subunits, e.g., three αHL monomer subunits and a concatemer subunit of four αHL monomers. The αHL pores retain the ability to identify nucleotide tags as the nucleotides are incorporated into a new polynucleotide strand by a polymerase that is attached to the αHL pore.

Apparatus Set-Up

The nanopore may be formed or otherwise embedded in a membrane disposed adjacent to a sensing electrode of a sensing circuit, such as an integrated circuit. The integrated circuit may be an application specific integrated circuit (ASIC). In some examples, the integrated circuit is a field effect transistor or a complementary metal-oxide semiconductor (CMOS). The sensing circuit may be situated in a chip or other device having the nanopore, or off of the chip or device, such as in an off-chip configuration. The semiconductor can be any semiconductor, including, without limitation, Group IV (e.g., silicon) and Group III-V semiconductors (e.g., gallium arsenide). See, for example, WO 2013/123450, for the apparatus and device set-up for sensing a nucleotide or tag.

Pore based sensors (e.g., biochips) can be used for electro-interrogation of single molecules. A pore based sensor can include a nanopore of the present disclosure formed in a membrane that is disposed adjacent or in proximity to a sensing electrode. The sensor can include a counter electrode. The membrane includes a trans side (i.e., side facing the sensing electrode) and a cis side (i.e., side facing the counter electrode).

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); kg (kilograms); µg (micrograms); L (liters); ml (milliliters); µl (microliters); cm (centimeters); mm (millimeters); µm (micrometers); nm (nanometers); ° C. (degrees Centigrade); h (hours); min (minutes); sec (seconds); msec (milliseconds).

EXAMPLES

The present invention is described in further detail in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

Example 1

Expression and Recovery

This example illustrates the expression and recovery of protein from bacterial host cells, e.g., *E. coli*.

DNA encoding the wild-type α-HL was purchased from a commercial source. The sequence was verified by sequencing.

Plasmid Construction.

The gene encoding either a wild-type or variant α-hemolysin was inserted into a pPR-IBA2 plasmid (IBA Life Sciences, Germany) under the control of T7 promoter.

Transformation.

*E. coli* BL21 DE3 (from Life Technologies) cells were transformed with the expression vector comprising the DNA encoding the wild-type or variant α-hemolysin using techniques well known in the art. Briefly, the cells were thawed on ice (if frozen). Next, the desired DNA (in a suitable vector/plasmid) was added directly into the competent cells (should not exceed 5% of that of the competent cells) and mixed by flicking the tube. The tubes were placed on ice for 20 minutes. Next, the cells were placed in a 42° C. water bath for 45 seconds without mixing, followed by placing the tubes on ice for 2 min. The cells were then transferred to a 15 ml sterilized culture tube containing 0.9 ml of SOC medium (pre-warmed at room temperature) and cultured at 37° C. for 1 hr in a shaker. Finally, an aliquot of the cells was spread onto a LB agar plate containing the appropriate antibiotic and the plates incubated at 37° C. overnight.

Protein Expression.

Following transformation, colonies were picked and inoculated into a small volume (e.g., 3 ml) of growth medium (e.g., LB broth) containing the appropriate antibiotic with shaking at 37° C., overnight.

The next morning, 1 ml of the overnight culture was transferred to a new 100 ml of autoinduction medium, e.g., Magic Media (Life Technologies) containing an appropriate antibiotic to select the expression plasmid. The culture was grown with shaking at 25° C. approximately 16 hrs but this depended on the expression plasmids. Cells were harvested by centrifugation at 3,000 g for 20 min at 4° C. and stored at −80° C. until used.

Purification.

Cells were lysed via sonication. The alpha-hemolysin was purified to homogeneity by affinity column chromatography.

Example 2

T12 and/or N17 Variants

The following example details the introduction of a mutation at a desired residue.

Mutations.

Site-directed mutagenesis was carried out using a QuikChange Multi Site-Directed Mutagenesis kit (Stratagene, La Jolla, Calif.) to prepare the T12 and/or N17 variants of SEQ ID NO:3.

The variants were expressed and purified as in Example 1.

Example 3

Assembly of Nanopore

This example describes the assembly of a nanopore comprising six α-HL variant subunits and one wild-type subunit.

The wild-type α-HL was expressed as described in Example 1 with SpyTag and a HisTag and purified on a cobalt affinity column using a cobalt elution buffer (200 mM NaCl, 300 mM imidazole, 50 mM Tris, pH 8). The desired α-HL variant was expressed as described in Example 1 with a StrepTag and purified using a Streptactin affinity column on the fast protein liquid chromatography (FPLC) using an elution buffer (50 mM tris, 5 mM desthiobiotin, 200 mM NaCl, pH 8). The proteins were stored at 4° C. if used within 5 days, otherwise 8% trehalose was added and the proteins were stored at −80° C.

Using approximately 20 mg of total protein, the wild-type α-HL and desired α-HL variant solutions were mixed together at the 1:6 ratio. Diphytanoylphosphatidylcholine (DPhPC) lipid was solubilized in 50 mM Tris, 200 mM NaCl, pH 8 or 150 mM KCl, 30 mM HEPES, pH 7.5 to a final concentration of 50 mg/ml and added to the mixture of α-HL monomers to a final concentration of 5 mg/ml. The mixture of the α-HL monomers was incubated at 40° C. for at least 10 min. The lipid hemolysin mixture was applied to a size-exclusion chromatography column to separate the lipid from the oligomerized proteins.

Example 4

Attachment of a Polymerase

This example provides for the attachment of a polymerase to a nanopore.

The polymerase may be coupled to the nanopore by any suitable means. See, for example, PCT/US2013/068967 (published as WO2014/074727; Genia Technologies), PCT/US2005/009702 (published as WO2006/028508), and PCT/US2011/065640 (published as WO2012/083249; Columbia Univ).

The polymerase, e.g., phi29 DNA Polymerase, was coupled to a protein nanopore (e.g., alpha-hemolysin), through a linker molecule. Specifically, the SpyTag and SpyCatcher system, that spontaneously forms covalent isopeptide linkages under physiological conditions was used. See, for example, Li et al, J Mol Biol. 2014 Jan. 23; 426(2):309-17.

The Sticky phi29 SpyCatcher HisTag was expressed according to Example 1 and purified using a cobalt affinity column. The SpyCatcher polymerase and the SpyTag oligomerized protein were incubated overnight at 4° C. in 3 mM $SrCl_2$. The 1:6-polymerase-template complex was then purified using size-exclusion chromatography.

Example 5

Activity of the Variants

This example shows the activity of the nanopores as provided by Examples 3 and 4 (nanopores with an attached polymerase).

The wild-type and variant nanopores were assayed to determine the effect of a mutation at one or more positions. The assay was designed to measure the time it takes to capture a tagged molecule by a DNA polymerase attached to the nanopore using alternating voltages, i.e., squarewaves.

The bilayers were formed and pores were inserted as described in PCT/US14/61853 filed 23 Oct. 2014. The nanopore device (or sensor) used to detect a molecule (and/or sequence a nucleic acid) was set-up as described in WO2013/123450.

To measure the time it takes to capture a tagged nucleotide by a DNA polymerase in our sequencing complex we have devised an assay that uses alternating positive and negative voltages (squarewaves) to determine the amount of time this takes. Our sequencing complex is comprised of a protein nanopore (αHL), which is attached to a single DNA polymerase (see Example 4). The tagged nucleotides are negatively charged, and are therefore attracted to the nanopore when the voltage applied is positive in nature, and repelled when the voltage applied to the nanopore sequencing complex is negative. We can thus measure the time it takes for a tag to thread into the pore by cycling the voltage between positive and negative potentials and determine how much time the nanopore's current is unobstructed (open channel) verses when the tag is threaded (reduced current flux).

To carry out this "time-to-thread" assay the Genia Sequencing device is used with a Genia Sequencing Chip. The electrodes are conditioned and phospholipid bilayers are established on the chip as explained in PCT/US2013/026514. Genia's sequencing complex is inserted to the bilayers following the protocol described in PCT/US2013/026514 (published as WO2013/123450).

The time-to-thread data shown in this example was collected using a buffer system comprised of 20 mM HEPES pH 7.5, 300 mM KCl, 3 uM tagged nucleotide, 3 mM $Ca^{2+}$, with a voltage applied of +/−100 mV with a duty cycle of 5 Hz. After the data was collected it was analyzed for squarewaves that showed the capture of a tagged nucleotide (threaded level) which lasted to the end of the positive portion of the squarewave, and was followed by another tag capture on the subsequent squarewave. The time-to-thread was measured by determining how long the second squarewave reported unobstructed open channel current. As an example, if 10 consecutive squarewaves showed tagged nucleotide captures that lasted to the end of the positive portion of the squarewave then the time-to-thread parameter would be calculated from squarewaves 2-10 (the first squarewave does not factor into the calculation because the polymerase did not have a tag bound to it in the previous squarewave). These time-to-thread numbers were then collected for all of the pores in the experiment and statistical parameters extracted from them (such as a mean, median, standard deviation etc.).

Results are shown in FIGS. 1A-1B, 2A-2B, 3A-3B, 4A-4B, and 5A-5B.

Example 6

Breaking Mutations in Oligomerization-Deficient Subunits

This example shows that breaking mutations prevent or reduce self-oligomerization of the αHL monomer subunits.

Site-directed mutagenesis was carried out using a QuikChange Multi Site-Directed Mutagenesis kit (Stratagene, La Jolla, Calif.) to introduce single amino acid mutations at each of first (site 1) and second (site 2) oligomerization domains of the α-hemolysin variant comprising the N17K mutation described in Example 2.

DNA polynucleotides encoding hemolysin variant N17K monomers further comprising one of mutations: H35D, D24A+V26D+K37S, H35E, H35L, H35I, T233R+S99K, Y101 D, Y101H, H35N, and T233R+S99K+D24A+V26D+K37S in the first or second oligomerization domain of the N17K variant, were cloned into pPR-IBA2 plasmids, expressed in *E. coli*, and subsequently purified as described in Example 1.

The purified mutated N17K variant monomers were reconstituted in the presence of lipid to determine the ability of each of the mutations in inhibiting the monomers from self-oligomerizing. 5 mg/mL DoPhPC Lipid was added to protein at a concentration of 1 mg/ml, and the mixture was incubated at 30° C. for 30 minutes. Liposomes were solubilized with 5% β-OG. The presence or absence of monomers and oligomers of each mutated variant was determined by subjecting the reconstituted mutated variant to SDS- PAGE gel electrophoresis. The results are shown in the gels of FIGS. 8A and 8B, and lanes 4-7 of the gel shown in FIG. 13.

Figure 9:
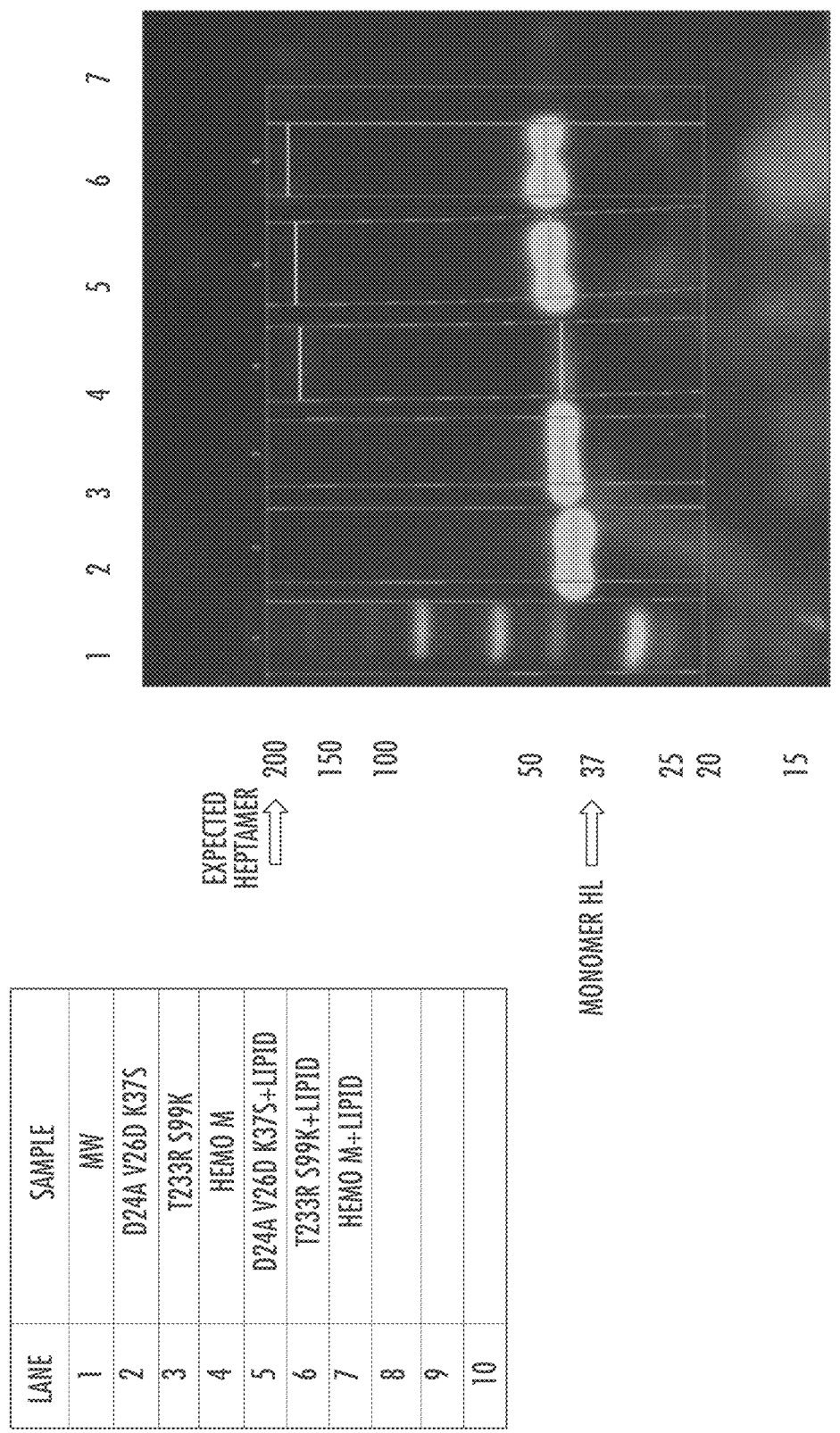
FIG. 9 shows a gel of αHL monomers with breaking mutations as indicated, and demonstrating that wild-type αHL monomer (Hemo M) does not enable oligomerization of the mutated monomers. Reference is made to Example 6.
Figures 10A, 10B, 10C:
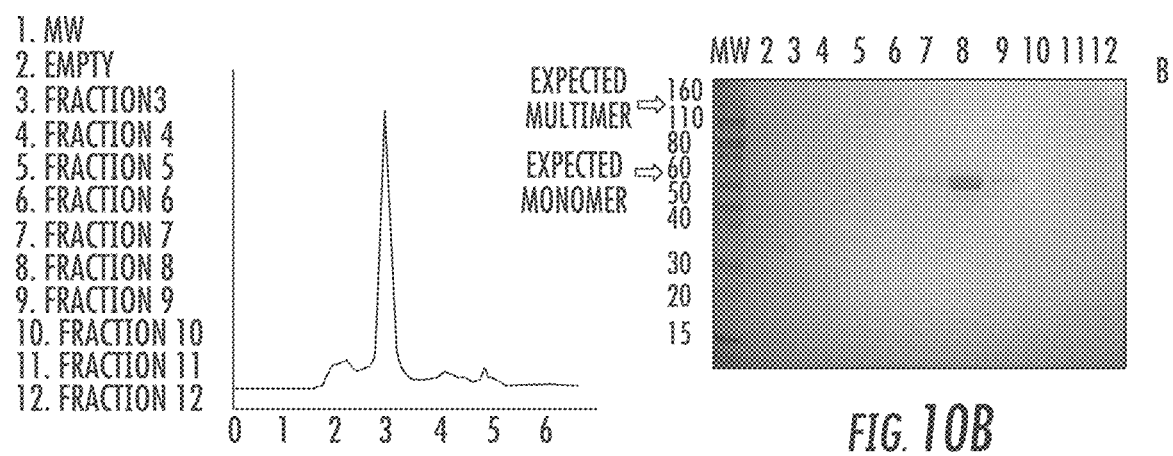
FIGS. 10A-10C show a chromatogram of a SEC purification of a subunit concatemer of two αHL monomers (10A) and SDS-PAGE gel (10B) of αHL concatemer of two monomers linked by $(GS)_5$ (SEQ ID NO:9), tagged at the N-terminus with His6-SpyTag ("His6" disclosed as SEQ ID NO: 10), and expressed with signal sequence pelB (10C). Reference is made to Example 7.
Figure 11:
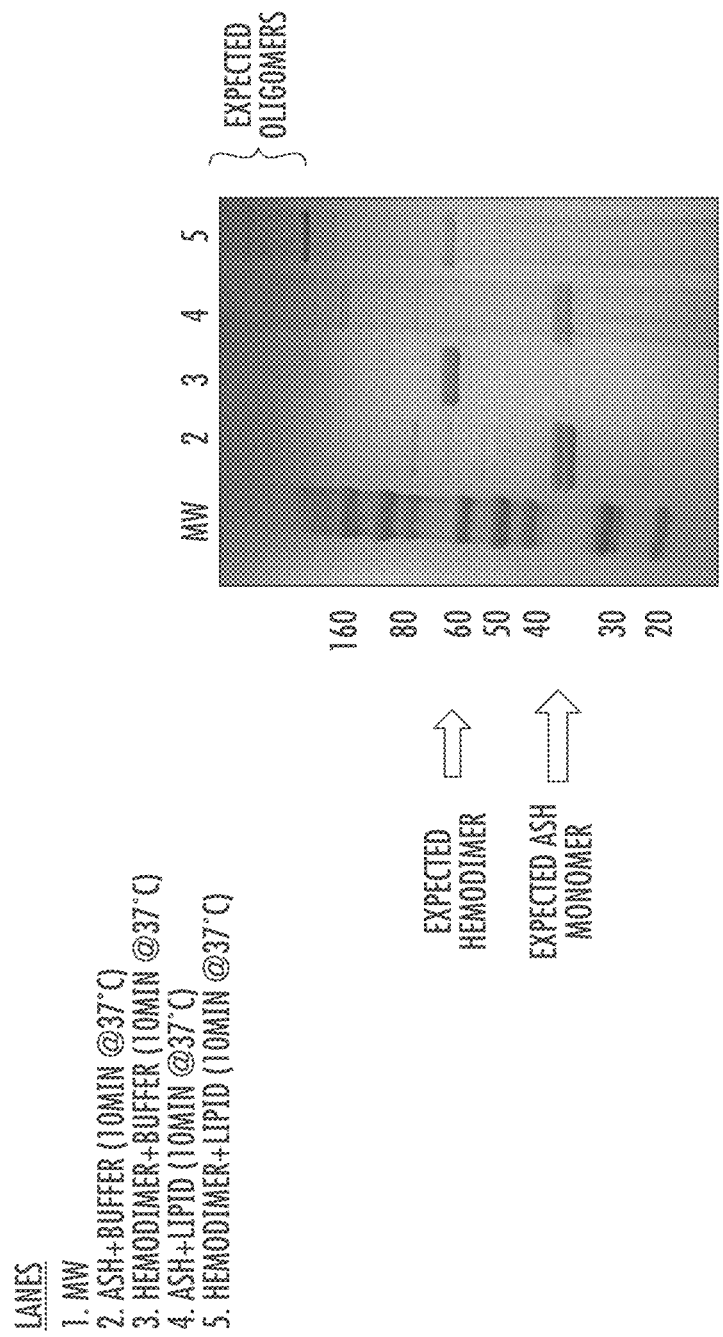
FIG. 11 shows an image of an SDS-PAGE gel that demonstrates that the concatemer of two monomers shown in FIG. 11 can oligomerize as seen as the high molecular weight bands in lane 5. Reference is made to Example 7.
Figure 12:
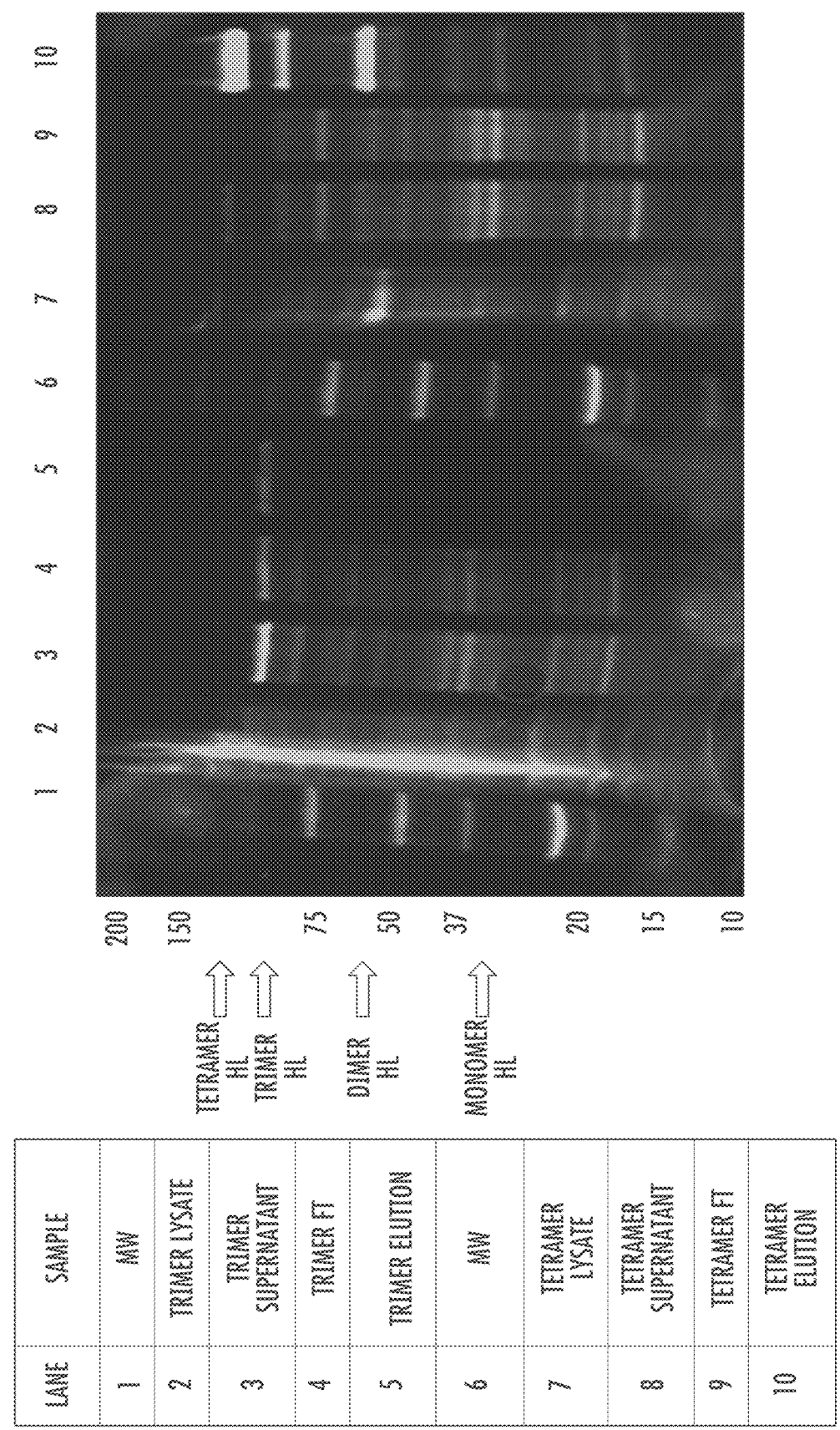
FIG. 12 shows an image of an SDS-PAGE gel demonstrating that concatenated subunits of three and four linked monomers can be expressed and purified. Reference is made to Example 8.

To test whether the breaking mutations could be rescued by wild-type αHL monomer (Hemo M), Hemo M was added in a 1:1 ratio to monomers with mutations D24A+V26D+ K37S, and T233R+S99K. The results shown in FIG. 9 demonstrate that these breaking mutations could not be rescued by wild-type monomer, i.e., the unmutated amino acids on either the first or second oligomerization domain on a wild-type monomer do not rescue the interaction of monomers having the mutations shown.

Additionally, the relative mobility (Rf) of mutated variant monomers/oligomers having mutations D24A+V26D+ K37S, T233R+S99K, H35E, H35D, H35N, and H35L were determined.

The results of the Rf values are shown in Table 1 below. The unmutated N17K variant monomer was determined to retain the ability to self-oligomerize, where 66.3% of the monomer was present as oligomers.

Taken together the data show that the breaking mutations made at one or both of the oligomerization domains (sites 1 and 2) of the hemolysin variant monomer, prevent or substantially reduce the ability of the monomer to self-oligomerize.

TABLE 1

Self-Oligomerization of mutated N17K variant monomers

| MUTANT | SELF-OLIGOMER | % SELF-OLIGOMER |
|---|---|---|
| D24A + V26D + K37S | − | 0 |
| T233R + S99K | − | 0 |
| H35E | − | 0 |
| H35D | − | 0 |
| H35N | − | 0 |
| H35L | + | 2.8 |

Example 7

Purification Reconstitution of Oligomerized Dimer Concatemers

This example demonstrates the formation of oligomers resulting from the oligomerization of a subunit comprising a concatemer of two wild-type αHL monomers.

A DNA polynucleotide encoding an αHL protein comprising a signal sequence, (pelB), a first αHL monomer, (Hemo 1), a linker (GS)5 (SEQ ID NO: 9), a second αHL monomer (Hemo 2), and a purification tag-attachment tag (His6-SpyTag) ("His6" disclosed as SEQ ID NO: 10), was cloned into pPR-IBA2 plasmids, expressed in *E. coli*, and subsequently purified as described in Example 1.

The purified concatemer dimer purifies as a single peak obtained by SEC (FIGS. 10A and 10B).

The purified concatemer was reconstituted in the presence of lipid by incubating the protein with DoPhPC lipid for 10 minutes at 37° C. The liposomes were solubilized, and subjected to electrophoresis, as described in Example 6.

FIG. 11 shows that the αHL concatemer of two monomers has the ability of self-oligomerizing.

It is expected that introducing the breaking mutation, for example as those described for the monomer in Example 6, will abolish the ability of the dimer concatemer to self-oligomerize, and may subsequently be used to manage the stoichiometry and arrangement of αHL subunits into functional heptameric pores.

Example 8

Expression and Purification of Oligomerized Trimers and Tetramer Concatemers This example shows the expression and purification of concatemers of three and four αHL monomers.

Trimer and tetramer concatemer subunits of αHL monomers were expressed and purified as described for the dimer concatemer in Example 7. The polynucleotide encoding the trimer concatemer expresses the following oligomerization subunit: (pelB), a first αHL monomer, (Hemo 1), a linker (GS)5 (SEQ ID NO: 9), a second αHL monomer (Hemo 2), a linker (GS)5 (SEQ ID NO: 9), a third αHL monomer (Hemo 3), and a Strepll tag.

The polynucleotide encoding the tetramer concatemer expresses the following oligomerization subunit: signal sequence (pelB), a first αHL monomer, (Hemo 1), a linker (GS)5 (SEQ ID NO: 9), a second αHL monomer (Hemo 2), a linker (GS)5 (SEQ ID NO: 9), a third αHL monomer (Hemo 3), a linker (GS)5 (SEQ ID NO: 9), a fourth αHL monomer (Hemo 4), and a His-SpyTag.

The concatemers were expressed in *E. coli* and purified as described in Example 1, and then were subjected to electrophoresis.

FIG. 12 shows that concatenated subunits of three and four linked monomers can be expressed and purified. The dimers and monomers seen on the gel are the result of degradation that occurs during purification, and that can be minimized by introducing an affinity tag at the N-terminus of the concatemer in combination with a purification step using the N-terminal affinity tag.

Example 9

Functional Hetero-Oligomeric Alpha-Hemolysin Heptameric Nanopores

To determine the ability of subunit concatemers to form functional αHL pores, a first αHL concatemer subunit of three monomers is combined in the presence of lipid with a second αHL concatemer subunit of four monomers to provide a heptameric αHL pore.

A breaking mutation i.e., amino acid substitution, is introduced in each of the first and second oligomerization domains of the trimer and of tetramer concatemer subunits. Additionally, a cognate and/or rescue mutation is introduced as an amino acid substitution in the first oligomerization domain of the trimer and the tetramer concatemers. Mutations are generated using site-directed mutagenesis as described in Example 2. A polymerase is attached to each of the concatemer subunits using the method described in Example 4.

The activity of the nanopore is measured as described in Example 5.

The hetero-oligomeric α-hemolysin heptamer of two concatemer subunits retains the ability to form a heptameric nanopore in a lipid bilayer.

Example 10

Cognate Mutations Enable Oligomerization of Subunits

To demonstrate the ability of mutations in first and second oligomerization domains of αHL subunits, amino acid substitutions H35I and Y101H were made respectively in the first and second oligomerization domains of the variant N17K αHL monomers.

The mutated variant monomers were expressed in bacteria and purified as described in Example 6.

Figure 13:
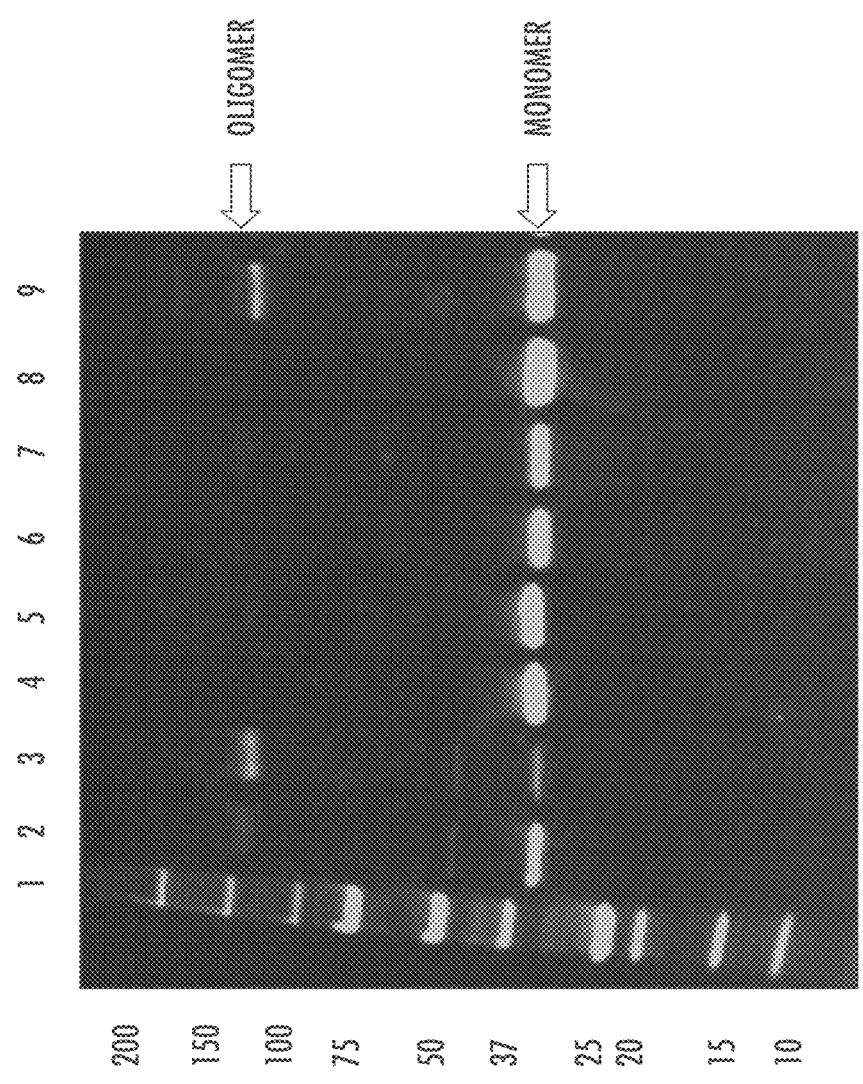
FIG. 13 shows an image of an SDS-PAGE gel that demonstrates oligomerization of αHL subunits having cognate mutations H35I and Y101H, which enable oligomerization of the mutated subunits. Reference is made to Example 10.

Next, the purified mutated N17K variant monomers were reconstituted in the presence of lipid to determine the ability of the mutations in the oligomerization domains in inhibiting or enabling oligomerization of the mutated variant monomers. 5 mg/mL DoPhPC Lipid was added to monomer protein at a concentration of 1 mg/ml, and the mixture was incubated at 30° C. for 30 minutes. Liposomes were solubilized with 5% β-OG. The presence or absence of monomers and oligomers of the mutated variant was determined by subjecting the reconstituted mutated variant to SDS-PAGE gel electrophoresis. The results are shown in FIG. 13.

Lanes 5 shows that mutation H35I alone inhibits oligomerization of the mutated variant monomers. Similarly, lane 7 shows that mutation Y101H alone also inhibits oligomerization, i.e., H35I and Y101H were shown to be breaking mutations. However, when both mutations H35I and Y101H were made on the variant monomers (lane 9), the ability of the mutated variant αHL monomers was restored, i.e., when paired, H35I and Y101H are cognate mutations that allow inter-subunit interaction and enable oligomerization of αHL monomers.

These data show that subunit interaction and oligomerization of αHL subunits, e.g., monomers, can be controlled by pairing of mutations made in the first and second oligomerization domains of subunits.

Example 11

Temperature-Dependent Conversion of Breaking Mutations

Experiments were performed to identify breaking mutations and corresponding rescue and/or cognate mutations that would enable oligomerization of subunits, Applicants unexpectedly discovered breaking mutations that can convert to their own cognate mutations at higher temperatures.

αHL monomers having an H35G mutation in the first oligomerization domain, were reconstituted in lipid at 25° C. and at 37° C. Reconstitution was performed as described in Example 10.

The results are shown in FIG. 14. Lane 2 shows that in the presence of lipid, monomers having the H35G mutation does not oligomerize at 25° C. Therefore, lane 2 shows that the H35G mutation is a breaking mutation that inhibits inter-subunit interaction, and oligomerization of the mutated subunits. However, as shown in lane 4, when the same mutated monomers were reconstituted in lipid at 37° C., oligomerization of the subunits was observed.

These data demonstrate that at higher temperatures, e.g., 37° C. versus 25° C., subunits having the H35G breaking mutation can oligomerize.

Therefore, in addition to pairing breaking mutations with cognate and/or rescue mutations to enable oligomerization of subunits, breaking mutations can be converted to their own cognate mutations and enable oligomerization.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entireties for all purposes.

SEQUENCE LISTING FREE TEXT

SEQ ID NO: 1 (WT αHL DNA)

```
ATGGCAGATC TCGATCCCGC GAAATTAATA CGACTCACTA TAGGGAGGCC     50
ACAACGGTTT CCCTCTAGAA ATAATTTTGT TTAACTTTAA GAAGGAGATA    100
TACAAATGGA TTCAGATATT AATATTAAAA CAGGTACAAC AGATATTGGT    150
TCAAATACAA CAGTAAAAAC TGGTGATTTA GTAACTTATG ATAAAGAAAA    200
TGGTATGCAT AAAAAAGTAT TTTATTCTTT TATTGATGAT AAAAATCATA    250
ATAAAAAATT GTTAGTTATT CGTACAAAAG GTACTATTGC AGGTCAATAT    300
AGAGTATATA GTGAAGAAGG TGCTAATAAA AGTGGTTTAG CATGGCCATC    350
TGCTTTTAAA GTTCAATTAC AATTACCTGA TAATGAAGTA GCACAAATTT    400
CAGATTATTA TCCACGTAAT AGTATTGATA CAAAAGAATA TATGTCAACA    450
TTAACTTATG GTTTTAATGG TAATGTAACA GGTGATGATA CTGGTAAAAT    500
TGGTGGTTTA ATTGGTGCTA ATGTTTCAAT TGGTCATACA TTAAAATATG    550
TACAACCAGA TTTTAAAACA ATTTTAGAAA GTCCTACTGA TAAAAAAGTT    600
GGTTGGAAAG TAATTTTTAA TAATATGGTT AATCAAAATT GGGGTCCTTA    650
TGATCGTGAT AGTTGGAATC CTGTATATGG TAATCAATTA TTTATGAAAA    700
CAAGAAATGG TTCTATGAAA GCAGCTGATA ATTTCTTAGA TCCAAATAAA    750
GCATCAAGTT TATTATCTTC AGGTTTTTCT CCTGATTTTG CAACAGTTAT    800
TACTATGGAT AGAAAAGCAT CAAAACAACA AACAAATATT GATGTTATTT    850
ATGAACGTGT AAGAGATGAT TATCAATTAC ATTGGACATC AACTAATTGG    900
```

| | |
|---|---|
| AAAGGTACAA ATACTAAAGA TAAATGGACA GATAGAAGTT CAGAAAGATA | 950 |
| TAAAATTGAT TGGGAAAAAG AAGAAATGAC AAATGGTCTC AGCGCTTGGA | 1000 |
| GCCACCCGCA GTTCGAAAAA TAA | 1023 |

SEQ ID NO: 2 (WT αHL amino acids) [as expressed in *E. coli*]
| | |
|---|---|
| MADSDINIKT GTTDIGSNTT VKTGDLVTYD KENGMHKKVF YSFIDDKNHN | 50 |
| KKLLVIRTKG TIAGQYRVYS EEGANKSGLA WPSAFKVQLQ LPDNEVAQIS | 100 |
| DYYPRNSIDT KEYMSTLTYG FNGNVTGDDT GKIGGLIGAN VSIGHTLKYV | 150 |
| QPDFKTILES PTDKKVGWKV IFNNMVNQNW GPYDRDSWNP VYGNQLFMKT | 200 |
| RNGSMKAADN FLDPNKASSL LSSGFSPDFA TVITMDRKAS KQQTNIDVIY | 250 |
| ERVRDDYQLH WTSTNWKGTN TKDKWTDRSS ERYKIDWEKE EMTNGLSAWS | 300 |
| HPQFEK | 306 |

SEQ ID NO: 3 (Mature WT αHL sequence for numbering)
| | |
|---|---|
| ADSDINIKTG TTDIGSNTTV KTGDLVTYDK ENGMHKKVFY SFIDDKNHNK | 50 |
| KLLVIRTKGT IAGQYRVYSE EGANKSGLAW PSAFKVQLQL PDNEVAQISD | 100 |
| YYPRNSIDTK EYMSTLTYGF NGNVTGDDTG KIGGLIGANV SIGHTLKYVQ | 150 |
| PDFKTILESP TDKKVGWKVI FNNMVNQNWG PYDRDSWNPV YGNQLFMKTR | 200 |
| NGSMKAADNF LDPNKASSLL SSGFSPDFAT VITMDRKASK QQTNIDVIYE | 250 |
| RVRDDYQLHW TSTNWKGTNT KDKWTDRSSE RYKIDWEKEE MTNGLSAWSH | 300 |
| PQFEK | 305 |

SEQ ID NO: 4 (N17K αHL amino acids)
| | |
|---|---|
| ADSDINIKTG TTDIGSKTTV KTGDLVTYDK ENGMHKKVFY SFIDDKNHNK | 50 |
| KLLVIRTKGT IAGQYRVYSE EGANKSGLAW PSAFKVQLQL PDNEVAQISD | 100 |
| YYPRNSIDTK EYMSTLTYGF NGNVTGDDTG KIGGLIGANV SIGHTLKYVQ | 150 |
| PDFKTILESP TDKKVGWKVI FNNMVNQNWG PYDRDSWNPV YGNQLFMKTR | 200 |
| NGSMKAADNF LDPNKASSLL SSGFSPDFAT VITMDRKASK QQTNIDVIYE | 250 |
| RVRDDYQLHW TSTNWKGTNT KDKWTDRSSE RYKIDWEKEE MTNGLSAWSH | 300 |
| PQFEK | 305 |

SEQ ID NO: 5 (N17R αHL amino acids)
| | |
|---|---|
| ADSDINIKTG TTDIGSRTTV KTGDLVTYDK ENGMHKKVFY SFIDDKNHNK | 50 |
| KLLVIRTKGT IAGQYRVYSE EGANKSGLAW PSAFKVQLQL PDNEVAQISD | 100 |
| YYPRNSIDTK EYMSTLTYGF NGNVTGDDTG KIGGLIGANV SIGHTLKYVQ | 150 |
| PDFKTILESP TDKKVGWKVI FNNMVNQNWG PYDRDSWNPV YGNQLFMKTR | 200 |
| NGSMKAADNF LDPNKASSLL SSGFSPDFAT VITMDRKASK QQTNIDVIYE | 250 |
| RVRDDYQLHW TSTNWKGTNT KDKWTDRSSE RYKIDWEKEE MTNGLSAWSH | 300 |
| PQFEK | 305 |

SEQ ID NO: 6 (T12K αHL amino acids)
| | |
|---|---|
| ADSDINIKTG TKDIGSNTTV KTGDLVTYDK ENGMHKKVFY SFIDDKNHNK | 50 |
| KLLVIRTKGT IAGQYRVYSE EGANKSGLAW PSAFKVQLQL PDNEVAQISD | 100 |
| YYPRNSIDTK EYMSTLTYGF NGNVTGDDTG KIGGLIGANV SIGHTLKYVQ | 150 |
| PDFKTILESP TDKKVGWKVI FNNMVNQNWG PYDRDSWNPV YGNQLFMKTR | 200 |
| NGSMKAADNF LDPNKASSLL SSGFSPDFAT VITMDRKASK QQTNIDVIYE | 250 |

SEQUENCE LISTING FREE TEXT

```
RVRDDYQLHW TSTNWKGTNT KDKWTDRSSE RYKIDWEKEE MTNGLSAWSH        300

PQFEK                                                        305

SEQ ID NO: 7 (T12R αHL amino acids)
ADSDINIKTG TRDIGSNTTV KTGDLVTYDK ENGMHKKVFY SFIDDKNHNK         50

KLLVIRTKGT IAGQYRVYSE EGANKSGLAW PSAFKVQLQL PDNEVAQISD        100

YYPRNSIDTK EYMSTLTYGF NGNVTGDDTG KIGGLIGANV SIGHTLKYVQ        150

PDFKTILESP TDKKVGWKVI FNNMVNQNWG PYDRDSWNPV YGNQLFMKTR        200

NGSMKAADNF LDPNKASSLL SSGFSPDFAT VITMDRKASK QQTNIDVIYE        250

RVRDDYQLHW TSTNWKGTNT KDKWTDRSSE RYKIDWEKEE MTNGLSAWSH        300

PQFEK                                                        305

SEQ ID NO: 8 (Mature WT aHL; AAA26598)
ADSDINIKTG TTDIGSNTTV KTGDLVTYDK ENGMHKKVFY SFIDDKNHNK         50

KLLVIRTKGT IAGQYRVYSE EGANKSGLAW PSAFKVQLQL PDNEVAQISD        100

YYPRNSIDTK EYMSTLTYGF NGNVTGDDTG KIGGLIGANV SIGHTLKYVQ        150

PDFKTILESP TDKKVGWKVI FNNMVNQNWG PYDRDSWNPV YGNQLFMKTR        200

NGSMKAADNF LDPNKASSLL SSGFSPDFAT VITMDRKASK QQTNIDVIYE        250

RVRDDYQLHW TSTNWKGTNT KDKWTDRSSE RYKIDWEKEE MTN              293
```

CITATION LIST

Patent Literature

[1] PCT/US2013/026514 (published as WO2013/123450) entitled "Methods for Creating Bilayers for Use with Nanopore Sensors"
[2] PCT/US2013/068967 (published as WO 2014/074727) entitled "Nucleic Acid Sequencing Using Tags"
[3] PCT/US14/61853 filed 23 Oct. 2014 entitled "Methods for Forming Lipid Bilayers on Biochips"

Non-Patent Literature

[4] Aksimentiev and Schulten, *Imaging α-Hemolysin with Molecular Dynamics: Ionic Conductance, Osmotic Permeability, and the Electrostatic Potential Map*, Biophysical Journal (2005) 88: 3745-3761.
[5] Butler et al., *Single-molecule DNA detection with an engineered MspA protein nanopore*, PNAS (2008) 105 (52): 20647-20652.
[6] Korchev et al., *Low Conductance States of a Single Ion Channel are not 'Closed'*, J. Membrane Biol. (1995) 147:233-239.
[7] Krasilnikov and Sabirov, *Ion Transport Through Channels Formed in Lipid Bilayers by Staphylococcus aureus Alpha-Toxin*, Gen. Physiol. Biophys. (1989) 8:213-222.
[8] Nakane et al., *A Nanosensor for Transmembrane Capture and Identification of Single Nucleic Acid Molecules*, Biophys. J. (2004) 87:615-621.
[9] Rhee and Burns, *Nanopore sequencing technology: nanopore preparations*, TRENDS in Biotech. (2007) 25(4):174-181.
[10] Song et al., *Structure of Staphylococcal α-Hemolysin, a Heptameric Transmembrane Pore*, Science (1996) 274: 1859-1866.
[11] Kasianowicz et al., *Nanometer-scale pores: potential applications for analyte detection and DNA characterization*, Proc. Natl. Acad. Sci. USA (1996) 93:13770-13773.
[12] Akeson et al., *Microsecond timescale discrimination among polycytidylic acid, polyadenylic acid, and polyuridylic acid as homopolymers or as segments within single RNA molecules*, Biophys. J. (1999) 77:3227-3233.
[13] Meller et al., *Voltage-driven DNA translocations through a nanopore*, Phys. Rev. Lett., 86 (2001), pp. 3435-3438.
[14] Howorka et al., *Sequence-specific detection of individual DNA strands using engineered nanopores*, Nat. Biotechnol., 19 (2001a), pp. 636-639.
[15] Howorka et al., *Kinetics of duplex formation for individual DNA strands within a single protein nanopore*, Proc. Natl. Acad. Sci. USA, 98 (2001b), pp. 12996-13001.
[16] Movileanu et al., *Detecting protein analytes that modulate transmembrane movement of a polymer chain within a single protein pore*, Nat. Biotechnol., 18 (2000), pp. 1091-1095.
[17] Hammerstein et al., Subunit dimers of α-Hemolysin Expand the Engineering Toolbox for Protein nanopores, J. Biol. Chem. (2011) 286:14324-14334.
[18] Zakeri et al. Peptide tag forming a covalent bond to a protein, through engineering a bacterial adhesion, PNAS109:E690-E697 (2012).
[19] Dennler et al., Transglutaminase-based chemo-enzymatic conjugation approach yields homogenous antibody-drug conjugates, Bioconjug Chem 25:569-578 (2014).
[20] Thapa et al., Native Chemical Ligation: A boon to peptide chemistry, Molecules 19:14461-14483 [2014].
[21] Wu and Guo, Sortase-mediated transpeptidation for site-specific modification of peptides, glycopeptides, and proteins, J Carbohydr Chem 31:48-66 [2012].

[22] Heck et al., Enzyme-catalyzed protein crosslinking, Appl Microbiol Biotechnol 97:461-475 [2013].
[23] Rashidian et al., Chemoenzymatic labeling of proteins: techniques and approaches, Bioconjug Chem 24:1277-1294 [2013].

The entirety of each patent, patent application, publication, document, GENBANK sequence, website and other published material referenced herein hereby is incorporated by reference, including all tables, drawings, and figures. All patents and publications are herein incorporated by reference to the same extent as if each was specifically and individually indicated to be incorporated by reference. Citation of the above patents, patent applications, publications and documents is not an admission that any of the foregoing is pertinent prior art, nor does it constitute any admission as to the contents or date of these publications or documents. All patents and publications mentioned herein are indicative of the skill levels of those of ordinary skill in the art to which the invention pertains.

What is claimed is:

1. A hetero-oligomeric α-hemolysin (αHL) heptamer, comprising at least one preceding and at least one following subunit, each subunit comprising at least one αHL monomer and/or at least one polypeptide comprising concatenated αHL monomers,
   wherein the at least one αHL monomer and/or the at least one polypeptide comprising concatenated αHL monomers comprises a mutation corresponding to H35L of SEQ ID NO:3; and
   wherein the heptamer comprises exactly 7 αHL monomers, each αHL monomer comprising a first oligomerization domain and a second oligomerization domain, the first oligomerization domain of each αHL monomer being linked to the second oligomerization domain of a preceding αHL monomer and the second oligomerization domain of each αHL monomer being linked to the first oligomerization domain of a following αHL monomer.

2. The hetero-oligomeric αHL heptamer of claim 1, wherein at least one αHL monomer further comprises a time-to-thread (TTT) substitution at a position corresponding to one or both of position 12 and position 17 of SEQ ID NO: 3.

3. An isolated polypeptide comprising one or more alpha-hemolysin monomers, wherein at least one of the alpha-hemolysin monomers comprises an amino acid sequence having at least 85% sequence identity to SEQ ID NO: 3 and an H35L substitution.

4. The isolated polypeptide of claim 3, wherein one or more of the alpha-hemolysin monomers further comprise a time-to-thread (TTT) substitution at a position corresponding to position 12 and/or position 17 of SEQ ID NO: 3.

5. The isolated polypeptide of claim 4, wherein the TTT substitution is selected from the group consisting of T12K, T12R, N17K, and N17R.

6. The isolated polypeptide of claim 3 having one alpha-hemolysin monomer.

7. The isolated polypeptide of claim 3 having at least two alpha-hemolysin monomers, wherein each monomer of the polypeptide is separated from each adjacent monomer in the polypeptide by a flexible linker.

8. The isolated polypeptide of claim 7 having from two to seven alpha-hemolysin monomers.

9. The isolated polypeptide of claim 3, wherein at least one of the one or more alpha-hemolysin monomers further comprises an attachment component.

10. The isolated polypeptide of claim 9, wherein the attachment component comprises a SpyTag or SpyCatcher peptide.

11. The isolated polypeptide of claim 9, wherein the attachment component joins the alpha-hemolysin monomer to a DNA polymerase, an RNA polymerase, or a reverse transcriptase.

12. A heptameric pore complex comprising seven alpha-hemolysin monomers, wherein at least one of the alpha-hemolysin monomers comprises an amino acid sequence having at least 85% sequence identity to SEQ ID NO: 3 and an H35L substitution.

13. The heptameric pore complex of claim 12, further comprising a polymerase linked to one of the alpha-hemolysin monomers.

14. The heptameric pore complex of claim 13, wherein the polymerase is covalently linked to the alpha-hemolysin monomer.

15. The heptameric pore complex of claim 12, wherein one or more of the alpha-hemolysin monomers further comprises a time-to-thread (TTT) substitution at a position corresponding to one or both of position 12 and position 17 of SEQ ID NO: 3.

16. The heptameric pore complex of claim 15, wherein the TTT substitution or substitutions is/are selected from the group consisting of T12K, T12R, N17K, and N17R.

17. The heptameric pore complex of claim 12, wherein each alpha-hemolysin monomer of the heptameric pore complex is disposed within a separate polypeptide from the other alpha-hemolysin monomers of the heptameric pore complex.

18. The heptameric pore complex of claim 12, wherein from two to seven of the alpha-hemolysin monomers of the heptameric pore complex are disposed within a single polypeptide.

19. The isolated polypeptide of claim 12, wherein at least one of the one or more alpha-hemolysin monomers further comprises an attachment component.

20. The isolated polypeptide of claim 19, wherein the attachment component comprises a SpyTag or SpyCatcher peptide.

21. The isolated polypeptide of claim 19, wherein the attachment component joins the alpha-hemolysin monomer to a DNA polymerase, an RNA polymerase, or a reverse transcriptase.

22. A method of making a heptameric pore complex, the method comprising heating a plurality of polypeptides of claim 3 in the presence of a lipid at a temperature greater than 25° C. for a sufficient period of time for the polypeptides to self-aggregate into alpha-hemolysin heptamers.

23. The method of claim 22, wherein the temperature at which the polypeptides are heated is 30° C. or higher.

24. The method of claim 23, wherein the temperature at which the polypeptides are heated is from 30° C. to 50° C.

25. A chip for nucleic acid sequencing, said chip comprising a heptameric pore complex of claim 12 disposed in a membrane adjacent to or in proximity to an electrode.

* * * * *